US011741931B2

(12) United States Patent
Donovan et al.

(10) Patent No.: US 11,741,931 B2
(45) Date of Patent: Aug. 29, 2023

(54) ELECTRONIC STETHOSCOPE DEVICE WITH NOISE CANCELLATION

(71) Applicant: Eko Devices, Inc., Oakland, CA (US)

(72) Inventors: Neal Donovan, Oakland, CA (US); Daniel Freschl, Oakland, CA (US); Eugene Gershtein, Oakland, CA (US); Philip Goolkasian, Oakland, CA (US); Connor Landgraf, Oakland, CA (US); Darius Mostowfi, Oakland, CA (US); Subramaniam Venkatraman, Oakland, CA (US); Jaclyn Leverett Wasson, Oakland, CA (US)

(73) Assignee: Eko Health, Inc., Emeryville, CA (US)

( * ) Notice: Subject to any disclaimer, the term of this patent is extended or adjusted under 35 U.S.C. 154(b) by 316 days.

(21) Appl. No.: 17/274,071

(22) PCT Filed: Sep. 23, 2020

(86) PCT No.: PCT/US2020/052192
§ 371 (c)(1),
(2) Date: Mar. 5, 2021

(87) PCT Pub. No.: WO2021/061754
PCT Pub. Date: Apr. 1, 2021

(65) Prior Publication Data
US 2022/0301537 A1     Sep. 22, 2022

Related U.S. Application Data

(60) Provisional application No. 62/903,943, filed on Sep. 23, 2019.

(51) Int. Cl.
A61B 7/04       (2006.01)
H04R 1/46      (2006.01)
(Continued)

(52) U.S. Cl.
CPC ...... *G10K 11/17823* (2018.01); *A61B 5/0002* (2013.01); *A61B 7/04* (2013.01);
(Continued)

(58) Field of Classification Search
CPC ........................................................ A61B 7/04
See application file for complete search history.

(56) References Cited

U.S. PATENT DOCUMENTS 5,492,129 A    2/1996  Greenberger
5,550,902 A    8/1996  Abbruscato
(Continued)

FOREIGN PATENT DOCUMENTS

JP    2003102725 A    4/2003

OTHER PUBLICATIONS

ISA Korean Intellectual Property Office, International Search Report and Written Opinion Issued in Application No. PCT/US2020/052192, dated Jan. 4, 2021, WIPO, 12 pages.

*Primary Examiner* — Ping Lee
(74) *Attorney, Agent, or Firm* — McCoy Russell LLP

(57) ABSTRACT

An electronic stethoscope device can be integrated into a conventional stethoscope to digitize auscultated sounds from the body of a patient. The device can be switched off so that the conventional stethoscope can be used as a standard stethoscope. When the device is switched on, the digitized auscultated sounds can be modified to remove the noise. Such modified sounds can be sent wirelessly from the electronic stethoscope device to a peripheral device that can receive such wireless signals, such as computer, cell phone, or cloud application, where the data can be viewed and manipulated further as desired.

13 Claims, 12 Drawing Sheets

(51) Int. Cl.
*G10K 11/178* (2006.01)
*A61B 5/00* (2006.01)
*H04R 1/02* (2006.01)

(52) U.S. Cl.
CPC .. *G10K 11/17827* (2018.01); *G10K 11/17873* (2018.01); *G10K 11/17885* (2018.01); *H04R 1/025* (2013.01); *H04R 1/46* (2013.01); *G10K 2210/116* (2013.01); *G10K 2210/3027* (2013.01); *H04R 2420/07* (2013.01)

(56) References Cited

U.S. PATENT DOCUMENTS

| | | | | |
|---|---|---|---|---|
| 5,610,987 A | * | 3/1997 | Harley | A61B 7/04 381/67 |
| 2004/0076303 A1 | * | 4/2004 | Vyshedskly | A61B 7/04 381/67 |
| 2004/0228494 A1 | | 11/2004 | Smith | |
| 2015/0156583 A1 | * | 6/2015 | Mulumudi | G10K 11/26 381/67 |
| 2015/0201272 A1 | | 7/2015 | Wong | |

* cited by examiner

ELECTRONIC STETHOSCOPE DEVICE WITH NOISE CANCELLATION

CROSS REFERENCE TO RELATED APPLICATIONS

The present application is a U.S. National Phase of International Patent Application No. PCT/US2020/052192, entitled "ELECTRONIC STETHOSCOPE DEVICE WITH NOISE CANCELLATION," filed on Sep. 23, 2020, which claims priority to U.S. Provisional Application No. 62/903,943, entitled "ELECTRONIC STETHOSCOPE DEVICE WITH NOISE CANCELLATION," and filed on Sep. 23, 2019. The entire contents of each of the above-identified applications are hereby incorporated by reference for all purposes.

BACKGROUND AND SUMMARY

This invention relates to the expanded use of mobile devices for medical applications. More specifically, it relates to acoustic stethoscopes that have been modified to function as digital, electronic stethoscopes, and whose modification includes active noise cancellation to enhance sounds detected by the stethoscope.

Auscultation, the process of listening to the internal sounds of the body, has historically been performed with acoustic stethoscopes. Many different forms of such a device have existed, most commonly with a two-sided chestpiece attached to hollow tubing that branched to two separate earpieces. Such devices use the diaphragm on one side of the chestpiece to transmit high frequency sounds to the earpieces, or a bell on the other side of the chestpiece to transmit low frequency sounds. However, the common acoustic stethoscope lacks the ability to digitize sounds that can be easily analyzed and shared electronically.

In recent years, many electronic stethoscope models have appeared in the art. Such devices largely resemble acoustic devices. A major difference between the two is that the standard chestpiece had been replaced with an electronic chestpiece that may include components for noise amplification, digital display, sound recording, and wireless signal transmission. In general, noise reduction and filtering are not part of such electronic chestpieces. Some models pair with a smartphone application to display images of recorded sounds that can later be edited and attached to medical records. Such computer-based medical records systems tend to be in competing, proprietary formats, reducing the ease with which doctors can collaborate over large distances.

What is needed is a simple, electronic component that can be used with any standard stethoscope and can perform the functions described above in a way that can be used with any proprietary medical records systems. It would be especially useful if such a component could also modify sound signals picked up by a stethoscope chestpiece to reduce or eliminate noise in the signals and to filter signals to focus only on body sounds of interest so that only the most useful information is transmitted and used for analysis.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The invention is illustrated in the figures of the accompanying drawings which are meant to be exemplary and not limiting, which like references are intended to refer to like or corresponding parts, and in which.

DETAILED DESCRIPTION

Figure 1A:
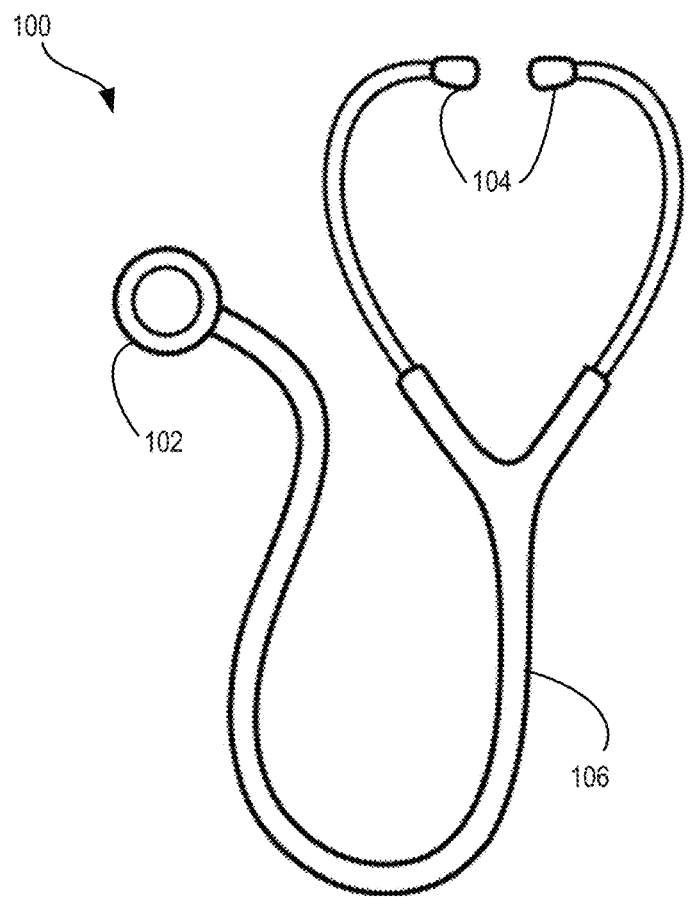
FIG. 1A is a schematic drawing showing a conventional stethoscope.

The term "noise cancellation" is used to include both adaptive noise cancellation and active noise cancellation.

In general, one listens to three main organs and organ systems during auscultation with the chestpiece of a stethoscope: the heart, the lungs, and the gastrointestinal system. Each organ or system has its own characteristic set of sounds. When auscultating the heart, abnormal sounds, including heart murmurs, gallops, and other extra sounds coinciding with heartbeats may be identified. Heart rate is often noted. When listening to lungs, breath sounds such as wheezes, rubs, and crackles may be identified. The gastrointestinal system may be auscultated to note the presence of bowel sounds such as swishing and gurgling. Each of these sounds has its own particular frequency, duration, quality, and intensity. It would be especially useful if one could filter out sounds that are not of interest when performing an examination. In one example, when auscultating the chest for information about lung condition, it would be useful if sounds coming from the heart could be eliminated from or suppressed in the signal.

Noise can also be a problem. When auscultating the body of a patient, it would be useful if noise could be eliminated. The term "noise" is used herein to describe any sound that has not originated from within the body of a patient. Such sounds may include, but are not limited to, ambient sound (e.g., background sounds from speech, air handling equipment, wind, water, birds, crowds, office noises, and traffic) and sound that may result from bumping or general handling of an electronic stethoscope device.

The term "electrical device" is used herein to include both ordinary electric devices and electronic devices. While an electric device is one that directly uses electrical energy to perform a task, electronic devices use electricity as the medium for manipulating information.

As discussed above, during auscultation, noise from the environment may interfere with the auscultation sounds from the body. Consequently, due to noise interference, a user may not be able identify or detect abnormal sounds during examination. One example approach to reduce environmental noise in an electronic stethoscope includes detecting environmental noise while also detecting auscultation sounds from the body. Therein, two microphones may be used, one for detecting the auscultation sounds and one for detecting the environmental noise.

However, the inventors herein recognize that the microphone that detects environmental noise may also sense the auscultation sounds. Consequently, the auscultation sounds are fed back as noise, which impacts a quality of auscultation sound output of the electronic stethoscope. Further, some electronic stethoscopes include a speaker to amplify and render processed auscultation sounds, and the output of the speaker may couple with the noise-detecting microphone, thereby exacerbating unwanted feedback of the auscultation sound through the noise-detecting microphone. Furthermore, due to the presence of air paths or airways in the stethoscope, auscultation sounds from the speaker and/or from the air path itself may travel more easily and couple with the noise-detecting microphone.

The inventors herein have recognized the above-mentioned issues, and have engineered a way to at least partially address them. In one example approach, an electronic stethoscope comprises a control unit including a first microphone, a second microphone, and an electronic acoustic modifier; an airway between an input tube and an output tube, the airway including a switching valve to switch between a digital mode of operation and an acoustic mode of operation of the electronic stethoscope; a chestpiece coupled to the input tube; a first port for transmission of auscultation sounds from the input tube to the first microphone, the first port coupling a portion of the airway between the switching valve and the input tube to the first microphone; a second port for transmission of ambient sounds from ambient to the second microphone, the second port and the second microphone mechanically isolated from the airway; wherein during the acoustic mode, the first microphone and the second microphone are unpowered; and wherein during the digital mode, the first microphone and the second microphone are electrically powered, and the electronic acoustic modifier generates a modified auscultation sound output based on a first auscultation sound input from the first microphone and a second noise input from the second microphone, and transmits the modified auscultation sound output to one or more audio interface outputs and/or a wireless transceiver.

In this way, by mechanically isolating the second microphone and the second port from the airway, coupling of auscultation sounds into an input of the second microphone is reduced, which in turn improves noise cancellation processing.

As an example, the electronic stethoscope may be constructed such that a thickness of the housing wall is greater on a side where the second port that fluidly couples to the environment and the second microphone are disposed. The greater thickness of the housing wall also provides isolation from a speaker that outputs a processed auscultation sound. Furthermore, a relative positioning of the second port and the second microphone with respect to the other components of the stethoscope including the first port to the first microphone, the first microphone, the speaker, and the airway, provides increased isolation of the second microphone from coupling with the auscultation sounds. Further still, during the digital mode of the operation, the switching valve is in a closed position, which blocks the airway, and prevents auscultation sounds from travelling continuously through the airway, which in turn provide an additional layer of mechanical isolation in tandem with the position of the second port to the second microphone and the housing thickness. Continuing on, during the digital mode of operation, only when the switching valve is closed, the electronic components including the first microphone, the second microphone, the electronic acoustic modifier (that performs the auscultation sound processing), and the speaker are electrically powered. Consequently, any inadvertent and unwanted coupling between inputs to the first microphone and the second microphone, and output from the speaker, is greatly reduced. All of the above mentioned features work in concert to provide improved noise-cancellation of the electronic stethoscope.

Figure 1B:
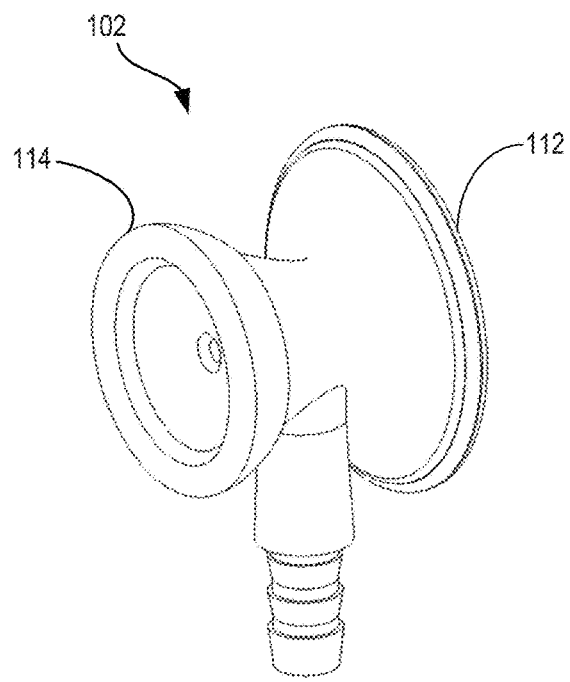
FIG. 1B is a schematic drawing showing a conventional stethoscope chestpiece.
Figure 2A:
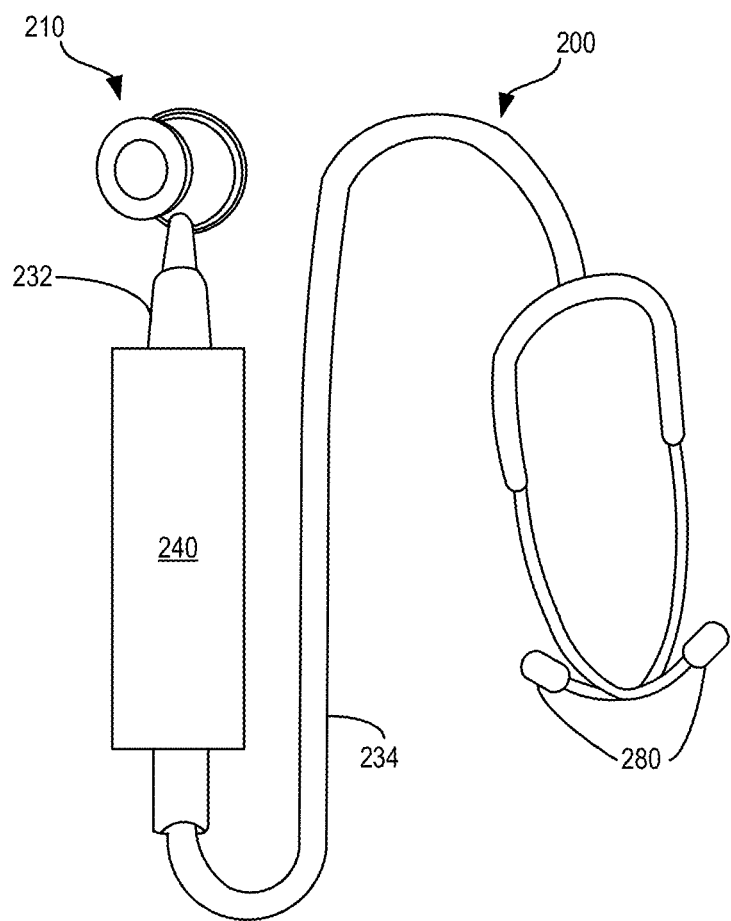
FIG. 2A is a schematic drawing showing a stethoscope with an electronic stethoscope device, according to an embodiment of the invention.
Figure 2B:
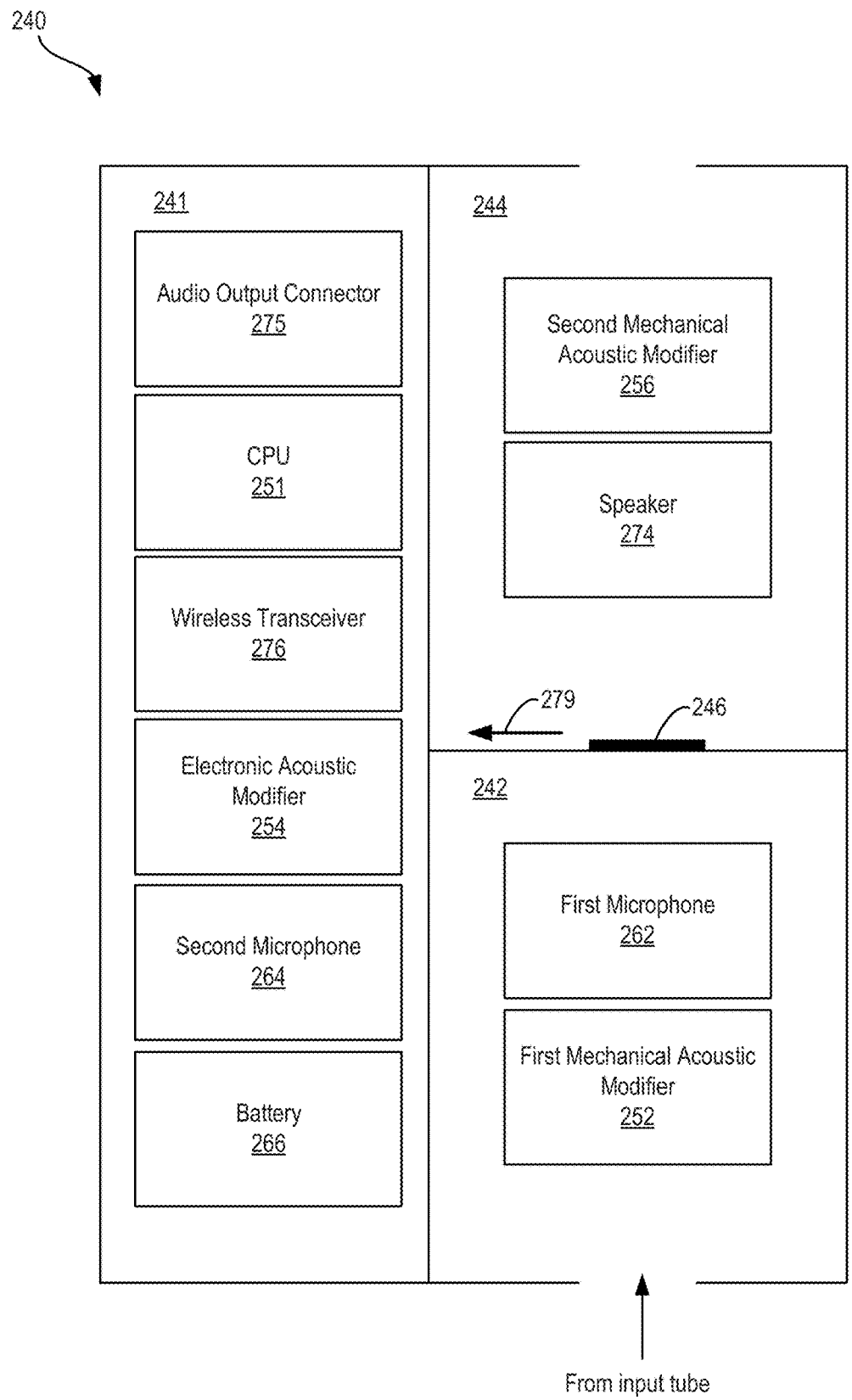
FIG. 2B is a block diagram showing the components of the electronic stethoscope device shown in FIG. 2A in a digital mode of operation, according to an embodiment of the invention.
Figure 2C:
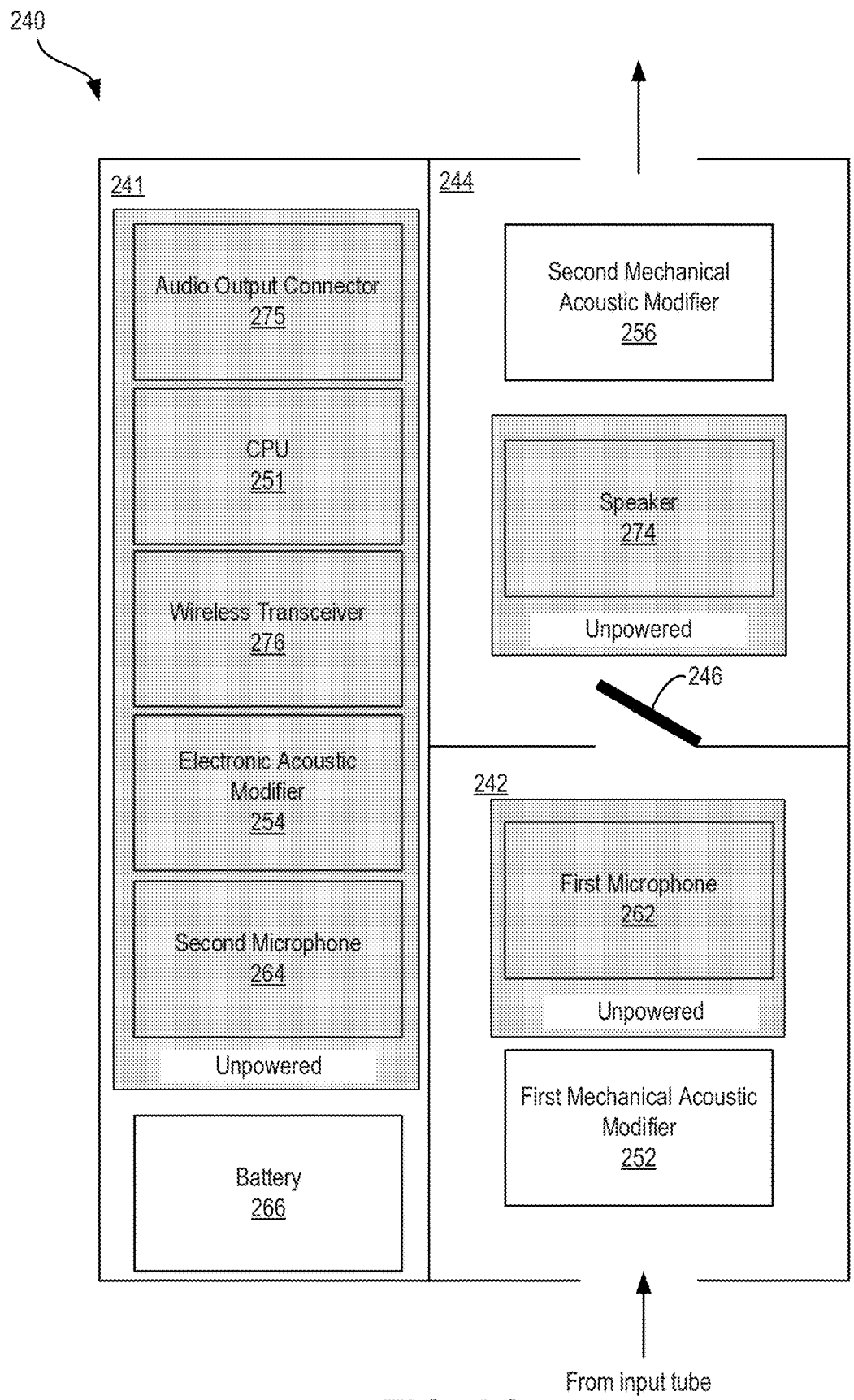
FIG. 2C is a block diagram showing the components of the electronic stethoscope device shown in FIG. 2A in an acoustic mode of operation, according to an embodiment of the invention.
Figure 2D:
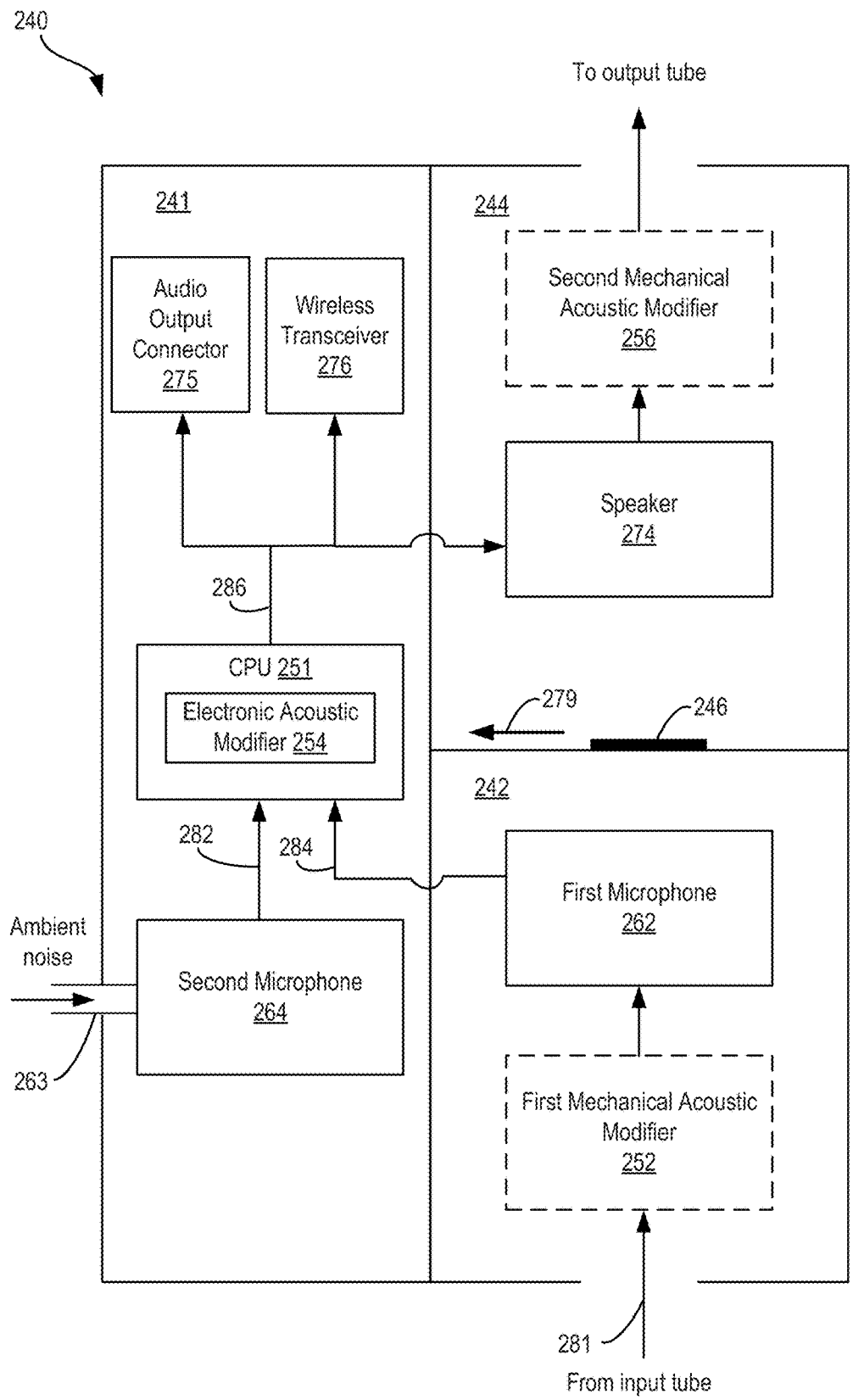
FIG. 2D is a block diagram showing signal flow during the digital mode of operation, according to an embodiment of the invention.

The present description relates to an electronic stethoscope, such as the example electronic stethoscope shown at FIG. 2A. A conventional stethoscope, such as the example conventional stethoscope shown at FIG. 1A, may be modified to function as an electronic stethoscope by including an electronic stethoscope device, such as the example electronic stethoscope device shown at FIG. 2A, between a chestpiece, such as the example chestpiece shown at FIG. 1B, and a tubing coupled to earpieces of the conventional stethoscope. The electronic stethoscope device may be operated in a digital mode, as shown in FIG. 2B or in an acoustic mode, as shown at FIG. 2C. Further, example input and output signals generated during the operation of the electronic stethoscope device in the digital mode is illustrated at FIG. 2D. Example methods for operating the electronic stethoscope are discussed at FIGS. 3A and 3B. The electronic stethoscope device may include one or more mechanical acoustic modifiers that may be used to filter auscultation sounds during the acoustic mode of operation while providing additional filtering of the auscultation sounds during the digital mode of operation. Examples of mechanical filters that may be used as mechanical acoustic modifiers are shown at FIGS. 4A-4E. Various views of an embodiment of the electronic stethoscope device are schematically illustrated at FIGS. 5A-5E. In particular, FIGS. 5A-5E show relative positioning of a first microphone and a second microphone, and mechanical isolation between the first and the second microphones that allow the electronic stethoscope device to provide improved noise cancelling function during the digital mode of operation.

The above advantages and other advantages and features of the present description will be readily apparent from the following detailed description when taken alone or in connection with the accompanying drawings.

FIG. 1A is a schematic drawing of a conventional stethoscope 100 that includes a chestpiece 102, earpieces 104 and tubing 106 connecting the chestpiece 102 and the earpieces 104. FIG. 1B shows the chestpiece 102 larger and in a perspective view. Many chestpieces 102 are two-sided; one side has a diaphragm 112 and the opposite side has a bell 114 that can pick up lower frequency sounds than can the diaphragm 112. As desired, either side of the chestpiece 102 can be pressed against a patient's body for auscultation, that is, for listening to sounds within the body. The chestpiece 102 may be of any size or shape sufficient to detect a patient's internal body sounds. It may be made of various materials, such as metal, rubber, plastic, and combinations thereof. Although the chestpiece 102 is usually circular, other shapes may be used.

In some embodiments of the invention, a conventional stethoscope can be modified to become an electronic stethoscope 200 by inserting into its tubing an electronic stethoscope device 240 that adds signal processing and other capabilities, as shown in the schematic drawing in FIG. 2A. The electronic stethoscope 200 includes a chestpiece 210, an input tube 232, the electronic stethoscope device 240, and an output tube 234. The chestpiece 210 is in acoustic communication with the electronic stethoscope device 240 through the input tube 232. The electronic stethoscope device 240 is in acoustic communication with earpieces 280 through the output tube 234.

In some embodiments of the invention, as shown in the schematic drawing in FIG. 2B, the electronic stethoscope device 240 includes a body 241 that includes various devices and an airway with two chambers therein. The electronic stethoscope device 240 has a first chamber 242 and a second chamber 244, both of which are configured to allow transmission of acoustic signals. There is a switching valve 246 between the first chamber 242 and the second chamber 244. When the switching valve 246 is open, acoustic signals can be transmitted between the first chamber 242 and the second chamber 244, and the electronic stethoscope is said to be in an acoustic mode of operation. When the switching valve 246 is closed, transmission of acoustic signals between the first chamber 242 and the second chamber 244 is blocked, and the electronic stethoscope is said to be in a digital mode of operation.

Figure 4A:
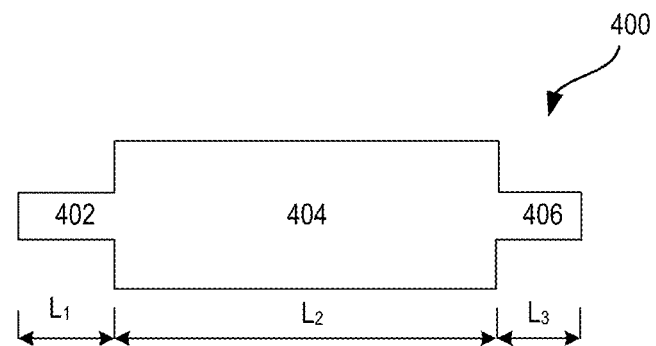
FIGS. 4A-4E show example mechanical acoustic filters that may be utilized in an electronic stethoscope device, according to various embodiments of the invention.

In some arrangements, the first chamber 242 contains a first mechanical acoustic modifier 252. In some arrangements, the first chamber 242 contains a first microphone 262. The first mechanical acoustic modifier 252 may be a mechanical acoustic filter. Examples of structures that can act as mechanical acoustic filters include, but are not limited to, vent holes whose size and shape are configured to filter specific frequency(ies), mass damper systems to compensate for acoustic overload, chamber shapes and sized that enhance acoustic resonance, foam mechanical filters that dampen certain frequencies, and chamber shapes and sizes that minimize impedance mismatches between, on the one hand, the input tube 232 and/or the output tube 234 and, on the other hand, the listener's ear. Examples of the first mechanical acoustic modifier 252 are shown at FIGS. 4A-4E. Turning to FIG. 4A, it shows a first mechanical acoustic filter 400. The first mechanical filter 400 may be a band pass filter, wherein a body of the filter 400 includes a first portion 402 having a first diameter and a first length L1, a second portion 404 having a second diameter and a second length L2, and a third portion 406 having a third diameter and a third length L3. Each of the first, second, and third portions 402, 404, and 406 respectively may be tubular with different diameters and different lengths. Further, the second portion 404 may positioned in between the first portion 402 and the third portion 406, and the second length L2 and the second diameter may be greater than lengths and diameters of the first and the third portions. In one example, the lengths L1, L2, and L3 may be different, and the first, second, and third diameters may be different to allow a desired audio frequency range to pass through while attenuating frequencies outside the desired audio frequency range. In some examples, a ratio of the diameters of the first, second, and third portions may be proportional to a ratio of the lengths of the first, second, and third portions.

Figure 4B:
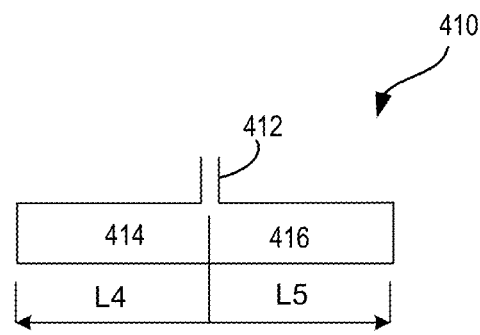

Next, FIG. 4B shows a second mechanical acoustic filter 410 that is configured as a high pass filter. The second mechanical acoustic filter 410 may include a port 412 perpendicular to a body of the filter 410, wherein the port 412 couples the body of the filter 410 with the atmosphere. The body of the filter 410 may further include a portion 414 and a portion 416, and the port 412 may be positioned centrally between the portion 414 and the portion 416. The portions may be tubular, and a diameter of the port 412 is less than a diameter of portion 414 and a diameter of portion 416. In one example, the diameters of the portions 414 and 416, and lengths L4 and L5 of the portions 414 and 416 respectively may be same.

Figure 4C:
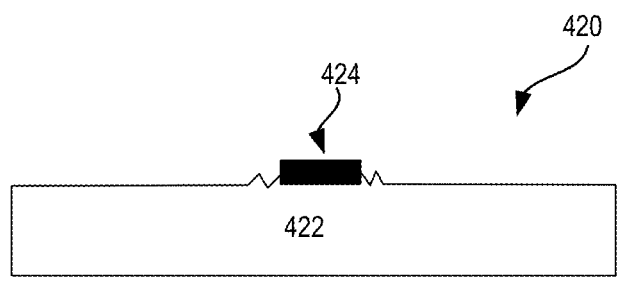

FIG. 4C shows a third mechanical acoustic filter 420 including a body 422 having a mass damper 424 for reducing vibrations. The third mechanical acoustic filter 420 with the mass damper 424 may provide high pass filtering function. While the present example shows a single mass damper, the filter may be modelled with more than one mass damper.

Figure 4D:
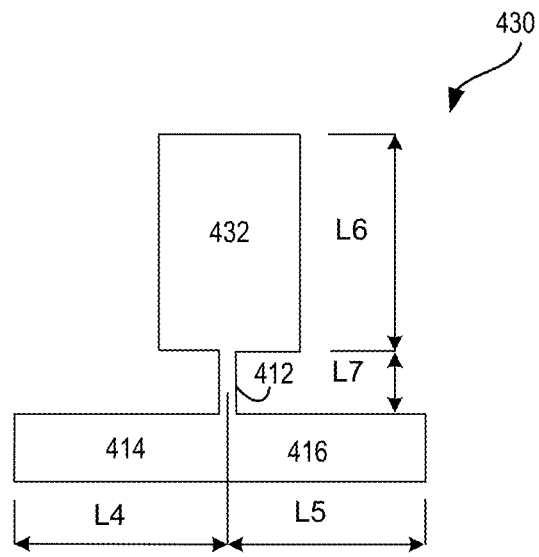

FIG. 4D shows a fourth mechanical acoustic filter 430 that is configured as a band pass filter. The filter 430 is has a body including a port similar to that of second mechanical acoustic filter 410 discussed at FIG. 4B. It may be noted that similar parts are labelled with same numbers, and description of such parts will not be repeated. The filter 430 further includes a side chamber 432 that is coupled to the port 412. In one example, a diameter of the side chamber 432 of the side chamber 432 is greater than the diameter of portion 414 and the diameter of the portion 416. Further, in some examples a length of the side chamber L6 may be greater than each of lengths L4 and L5, while a length L6 of the port 412 may be less than each of L4, L5, and L7.

Figure 4E:

Next, FIG. 4E shows a fifth mechanical acoustic filter 440 that may be configured with a greater body length to allow transmission of low frequency sounds, and thereby function as a low pass filter.

Returning to FIG. 2B, the first mechanical acoustic modifier 252 may include one or more of the mechanical acoustic filters or any combination of the mechanical acoustic filters discussed above. When there is no first mechanical acoustic modifier 252 in the first chamber 242, the first microphone 262 detects auscultated sound picked up by the chestpiece 210 and converts the auscultated sound into an auscultated electronic signal. When there is a first mechanical acoustic modifier 252 in the first chamber 242, it is positioned between an opening to the input tube and the first microphone 262. Thus, the auscultated sound picked up by the chestpiece 210 is modified by the first mechanical acoustic modifier 252 and then detected by the first microphone 262 which converts the auscultated sound into the auscultated electronic signal. In this way, the first mechanical acoustic modifier 252 reduces unwanted sound frequencies and improves sound output.

The electronic stethoscope device 240 includes a computer processing unit (CPU) 251, such as a microcontroller unit (MCU). The CPU 251 receives inputs and/or sends outputs to various electronic components (e.g., first microphone 262, electronic acoustic modifier 254, second microphone 264, battery 266, speaker 274, audio output connector 275, wireless transceiver 276) of the electronic stethoscope device 240. In some arrangements, there is one microdevice that contains the CPU and some or all of the electronic and electrical components. In some arrangements, the CPU, the electronic and electrical components are positioned on two or more microdevices.

The electronic stethoscope device 240 includes an electronic acoustic modifier 254 in the electronic stethoscope device 240 and in electrical communication with the CPU 251. In some arrangements, the electronic acoustic modifier 254 is a stand-alone device. In some arrangements, the electronic acoustic modifier 254 is firmware within the CPU 251 (as indicated in FIG. 2D). The electronic acoustic modifier 254 is configured to receive the auscultated electronic signal from the first microphone 262, to modify the auscultated electronic signal to form a modified electronic signal, and to transmit the modified electronic signal. Further discussion of the ways in which the electronic acoustic modifier 254 modifies the auscultated electronic signal can be found below.

In some arrangements, the CPU 251 can perform analysis on the auscultated electronic signal or on the modified electronic signal to extract information about the condition of the patient or to determine a preliminary diagnosis. In some arrangements, the CPU 251 can amplify the modified electronic signal before it is transmitted.

In some arrangements, there is a speaker (or electroacoustic transducer) 274 in the second chamber 244. The speaker 274 is configured to produce no sound when the electronic stethoscope is in the acoustic mode of operation (i.e., when the switching valve 246 is open). The speaker 274 is configured to receive the modified electronic signal from the electronic acoustic modifier 254 and to convert the modified electronic signal to modified sound for transmission to the output tube 234 when the electronic stethoscope device 240 is in the digital mode of operation (i.e., when the switching valve 246 is closed). In some arrangements, the speaker 274 is a piezo-based speaker or an acoustic resonator speaker. In some arrangements the speaker 274, sometimes in conjunction with the electronic acoustic modifier 254, is configured to amplify the modified sound so it is louder than the original auscultated sound. During the digital mode of operation, the modified sound output from the speaker 274 passes through an output portion of the airway between the switching valve 246 and the output tube 234 before it is transmitted to the ear pieces (e.g., ear pieces 280) via the output tube 234. The speaker 274 and the airway may be positioned within the electronic stethoscope device 240 such that the modified sound output from the speaker 274 does not couple to a second microphone 264 that senses noise from the environment. The details of arrangement and configuration of the various components of the electronic stethoscope device that provide improved noise cancellation of the auscultation sound are discussed below and with respect to FIGS. 5A-5E.

The electronic stethoscope device 240 includes an optional audio output connector 275, such as a headphone jack or USB-type port, which can receive the modified electronic signal from the electronic acoustic modifier 254. A user can physically connect a peripheral device to the audio output connector 275. Examples of such peripheral devices include but are not limited to, a computer, a cell phone, and a listening device configured to convert the modified electronic signal to sound.

In some arrangements, there is a wireless transceiver 276 in the electronic stethoscope device 240, in either the first chamber 242 or the second chamber 244. In some examples, the wireless transceiver 276 may be included in a circuit board, such as a PCB, that may also include one or more electronic components, such as the first microphone 262, the second microphone 264, and the CPU 251. The wireless transceiver 276 is in electrical communication with the electronic acoustic modifier 254. The wireless transceiver 276 is configured to receive the modified electronic signal from the electronic acoustic modifier 254, to convert the modified electronic signal to a modified wireless signal, and to wirelessly transmit the modified wireless signal from the electronic stethoscope. The wireless transceiver 276 may use any appropriate communication means and protocol, such as television, cellular phone, WiFi, satellite, two-way radio, infrared, short-range microwave signals, or IEEE 802.11 compliant radio signals. In some implementations, the wireless transceiver 276 may be configured to pair directly to an external device. Alternatively, the wireless transceiver 276 may communicate data to an external device through an intermediary device such as a wireless router maintaining a local area network (WLAN) or through the interne. The wireless transceiver 276 may also be configured to receive signals from one or more peripheral devices. In some arrangements, the wireless transceiver 276 is in electrical communication with the first microphone 262, and can wirelessly transmit the auscultated electronic signal.

As described above, the auscultated electronic signal or the modified electronic signal may be analyzed on the electronic stethoscope device 240 by the CPU 251. In some arrangements, the auscultated electronic signal or the modified electronic signal may be transmitted by the wireless transceiver 276 or through the audio output connector 275 to a peripheral device, such as a computer or a cell phone. Such signals can then be analyzed on the peripheral device to extract information about the condition of the patient or to determine a preliminary diagnosis. The results of such an analysis can be transmitted back to the wireless transceiver 276 and can be communicated to a user of the electronic stethoscope device 240 visually or with sound. Visual information can be provided using LEDs or other light sources or displays (not shown) on the electronic stethoscope device 240. Sound may be in the form of beeps, tones or voice transmitted through the speaker 274 or a secondary electrostatic transducer (not shown).

In some arrangements, there is a second mechanical acoustic modifier 256 near the exit of the electronic stethoscope device 240 where it joins the output tube 234. The second acoustic modifier 256 may be a mechanical acoustic filter. Examples of structures that can act as mechanical acoustic filters include, but are not limited to, vent holes whose size and shape are configured to filter specific frequency(ies), mass damper systems to compensate for acoustic overload, chamber shapes and sized that enhance acoustic resonance, foam mechanical filters that dampen certain frequencies, and chamber shapes and sizes that minimize impedance mismatches between, on the one hand, the input tube 232 and/or the output tube 234 and, on the other hand, the listener's ear. Examples of mechanical acoustic filters that may be utilized as the second mechanical acoustic modifier 256 are shown in FIGS. 4A-4E. The second mechanical acoustic modifier 256 may include one or more of the mechanical acoustic filters or any combination of the mechanical acoustic filters discussed above. Acoustic signals from the speaker 274 pass through the second acoustic modifier 256 before traveling through the output tube 234. The second acoustic modifier 256 further filters out unwanted sound frequencies, and works in concert with the noise cancellation processing performed by the electronic acoustic modifier 254 to improve auscultation sound output clarity and specificity.

The electronic stethoscope device 240 includes a second microphone 264 facing the external environment. The second microphone 264 is configured to detect noise and to convert the noise into an electronic noise signal. When such a second microphone 264 is included in the electronic stethoscope device 240, the electronic acoustic modifier 254 is configured to receive the electronic noise signal from the second microphone 264 and to use the electronic noise signal, for example, as part of active noise cancellation, in modifying the auscultated electronic signal to form the modified electronic signal. The second microphone 264 may sense noise from the environment via a port (as shown in FIG. 2D) that fluidly couples with the environment. The second microphone and the port to the second microphone may be positioned such that they are mechanically isolated from the airway, the speaker 274, as well as the first microphone 262. The mechanical isolation of the second microphone reduces coupling of the auscultation sounds that are output from the speaker, present within the airway and/or transmitted to the first microphone. As a result, unwanted feedback of auscultation sounds is reduced, noise cancellation processing is improved, and auscultation sound output clarity and specificity is improved.

In some arrangements, one or both of the first microphone 262 and the second microphone 264 is a MEMS microphone, an electret microphone, or a piezoelectric microphone.

Examples of the kinds of electronic signal modifications that are possible with the electronic acoustic modifier 254 include, but are not limited to, active noise cancellation, single channel noise reduction (SCNR), and upward or downward expansion. In an exemplary embodiment, active noise cancellation receives the electronic noise signal from the second microphone 264 and reduces the amplitude of or removes the noise component from the auscultated electronic signal, thus improving the quality of the modified electronic signal. SCNR refers to techniques which may reduce the noise portion of the modified electronic signal through the use of temporal, spectral or statistical differences between the original auscultated signal and noise. A downward expander can reduce the gain on a signal when the amplitude of a signal is below a pre-set threshold. In some arrangements, the gain is reduced to zero. Any gain reduction may minimize the detection of noise when the stethoscope is held against the air.

In some arrangements, the second microphone 264 can detect that the first microphone 262 is facing "open air" by comparing the signals coming from the two microphones. If the signals are highly correlated, the sounds that might be transmitted into the output tube can be suppressed. This would prevent amplification of sounds when the chestpiece is not on a patient and could prevent accidental exposure to extremely undesirable amplified sounds from such things as sirens, speech, doors closing, etc. If the two microphones detect significantly different sounds, it is an indication that the chestpiece may be on a surface intended to be auscultated, and amplification could be employed.

It should be understood that, in describing electrical communication, the phrase, "A is in electrical communication with B," describes both direct electrical communication from A and B or from B and A and also electrical communication that goes between A to B through the CPU, (i.e., from A to CPU to B and from B to CPU to A).

There is a battery 266 in the electronic stethoscope device 240. The battery 266 may be a primary battery or a secondary (rechargeable) battery. If the battery 266 is a primary battery, the outside of the electronic stethoscope device 240 has a door (not shown) through which the battery 266 can be changed. If the battery 266 is a secondary battery, the outside of the electronic stethoscope device 240 has a charging port (not shown) through which the battery 266 can be charged. The battery 266 is configured to supply power to the electronic components of the electronic stethoscope device 240, including, but not limited to, the first microphone 262, the electronic acoustic modifier 254, the second microphone 264, the speaker 274, and the wireless transceiver 276.

In some arrangements, the switching valve 246 acts also as an on/off switch for the electronic components of the electronic stethoscope device 240. When the switching valve 246 is open (acoustic mode), the electronic components are off. When the switching valve 246 is closed (digital mode), the electronic components are on. FIG. 2B shows the electronic stethoscope device 240 with the switching valve 246 in a closed position. When the switching valve 246 is in the closed position, an electrical connection is established for the various electronic components of the electronic stethoscope with a power source, such as the battery 266, which in turn results in current flow 279, thereby electrically powering the various electronic components that include but not limited to the first microphone 262, the second microphone 264, the speaker 274, the wireless transceiver 276, the CPU 251, the electronic acoustic modifier 254, and the audio output connector 275.

In some embodiments, wherein, one or more electronic components are arranged on the PCB, the circuit board may be electrically coupled to the switching valve 246 such that when the switching valve 246 is in the closed position during the digital mode of operation, the one or more electronic components on the circuit board may be electrically powered by the power source (e.g., battery 266) via the switching valve 246.

Turning to FIG. 2C, it shows the electronic stethoscope device 240 with the switching valve 246 in an open position. When the switching valve 246 is in the open position, the electronic components of the electronic stethoscope device 240 are unpowered, and the electronic stethoscope including the electronic stethoscope device operates in the acoustic mode, wherein the auscultation sound from the chestpiece is transmitted to the input tube, and from the input tube to the output tube via the airway that is continuous from the first chamber 242 to the second chamber 244 via an opening of the switching valve 246. When the switching valve 246 is open, electrical connection between the various electronic components and the power source is not established, and as such modification of the auscultation sound obtained via the chestpiece is performed via the first mechanical acoustic modifier 252 and/or the second mechanical acoustic modifier 256.

Further, when the switching valve 246 is in the closed position, the CPU 251 and/or the electronic acoustic modifier 254 processes the auscultation sound signals received from the first microphone 262. A high-level block diagram of the electronic stethoscope device 240 showing various signal inputs and outputs during the digital mode of operation when the switching valve 246 is in the closed position is shown at FIG. 2D.

Turning to FIG. 2D, the auscultation sound 281 from the input tube is transmitted to the first microphone 262 via the first mechanical acoustic modifier 252. In some examples, as discussed at FIGS. 5A-5E, a first port may fluidly couple the airway in the first chamber 242 with the first microphone 262. At the first microphone 262, the auscultation sound 281 is converted to auscultated sound signal 284, which is then transmitted to the CPU 251 and/or the electronic acoustic modifier 254 for further processing. Due to the closure of the switching valve 246, the auscultation sound 281 is not transmitted into the airway in the second chamber 244 from the airway in the first chamber 242. Further, a second port 263 fluidly couples the second microphone 264 to the ambient (alternatively referred to as environment), and thus, the second microphone 264 receives ambient noise via the second port 263. The second microphone generates a noise signal 282, which is transmitted to the CPU 251 and/or the electronic acoustic modifier 254.

The first port and the second port 263 are positioned such that the ports are mechanically isolated from each other. Further, the second port 263 is mechanically isolated from the speaker 274 and the airway in both the chambers 242 and 244. The first microphone 262 and the second microphone 264 are also mechanically isolated from each other. By mechanically isolating the second port 263 and the second microphone 264, from the airway, the speaker 274, and the first microphone, the auscultation sound is not fed into the second microphone 264, which improves noise-cancellation performed by the CPU and/or the electronic acoustic modifier 254. Additional details of mechanical isolation and relative positioning of the ports and the microphones are discussed with respect to FIGS. 5A-5E.

In this example at FIG. 2D, the electronic acoustic modifier 254 is shown included as a firmware on the CPU 251, and the auscultated sound signal 284 from the first microphone 262 is processed based on the noise signal 282 using executable instructions stored in a memory of the CPU 251 or the electronic acoustic modifier 254 or a combination thereof. The CPU and/or the electronic acoustic modifier 254 generates an output signal 286. The output signal 286 may be a noise-cancelled signal, for example.

The output signal 286 from the CPU 251 and/or the electronic acoustic modifier 254 is transmitted to one or more of the audio output connector 275 for subsequent rendering via a sound rendering device (e.g., ear phones) coupled via connecting wires to the audio output connector, the wireless transceiver 276 for wireless transmission to a device (e.g., mobile phone, computer, wireless ear plugs, etc.) wirelessly coupled to the electronic stethoscope device 240, and the speaker 274. Output from the speaker may be further mechanically processed by the second mechanical acoustic modifier 256 before subsequent transmission to the ear pieces (e.g., ear pieces 280) via the output tube 234.

In some embodiments of the invention, the electronic stethoscope device 240 includes one or more buttons or switches to receive user inputs, such as a power button or switch (not shown) with which to turn power on or activate the connection between the battery 266 and the electronic components, a button or switch to open and close the switching valve 246, a button or switch (not shown) for establishing a wireless connection between the wireless transceiver 276 and an outside receiver, a volume control (not shown) for the first microphone 262, and a volume control (not shown) for the second microphone 264. There may also be one or more display outputs (not shown) on the outside of the electronic stethoscope device 240, such as indicator lights. In some implementations a display screen configured to show words or images may also be included as display outputs. Indicator lights and/or display screens may provide information about the state of the electronic stethoscope device 240 and/or they may provide information about the condition of the patient.

In some embodiments of the invention, the electronic stethoscope device 240 includes one or more devices to provide audio indicator signals (not shown) to provide sounds, such as beeps or verbal language, to indicate device operation status and/or information about the condition of the patient. In some arrangements, the volume of the audio indicator can be adjusted or turned off through user inputs.

Figure 3A:
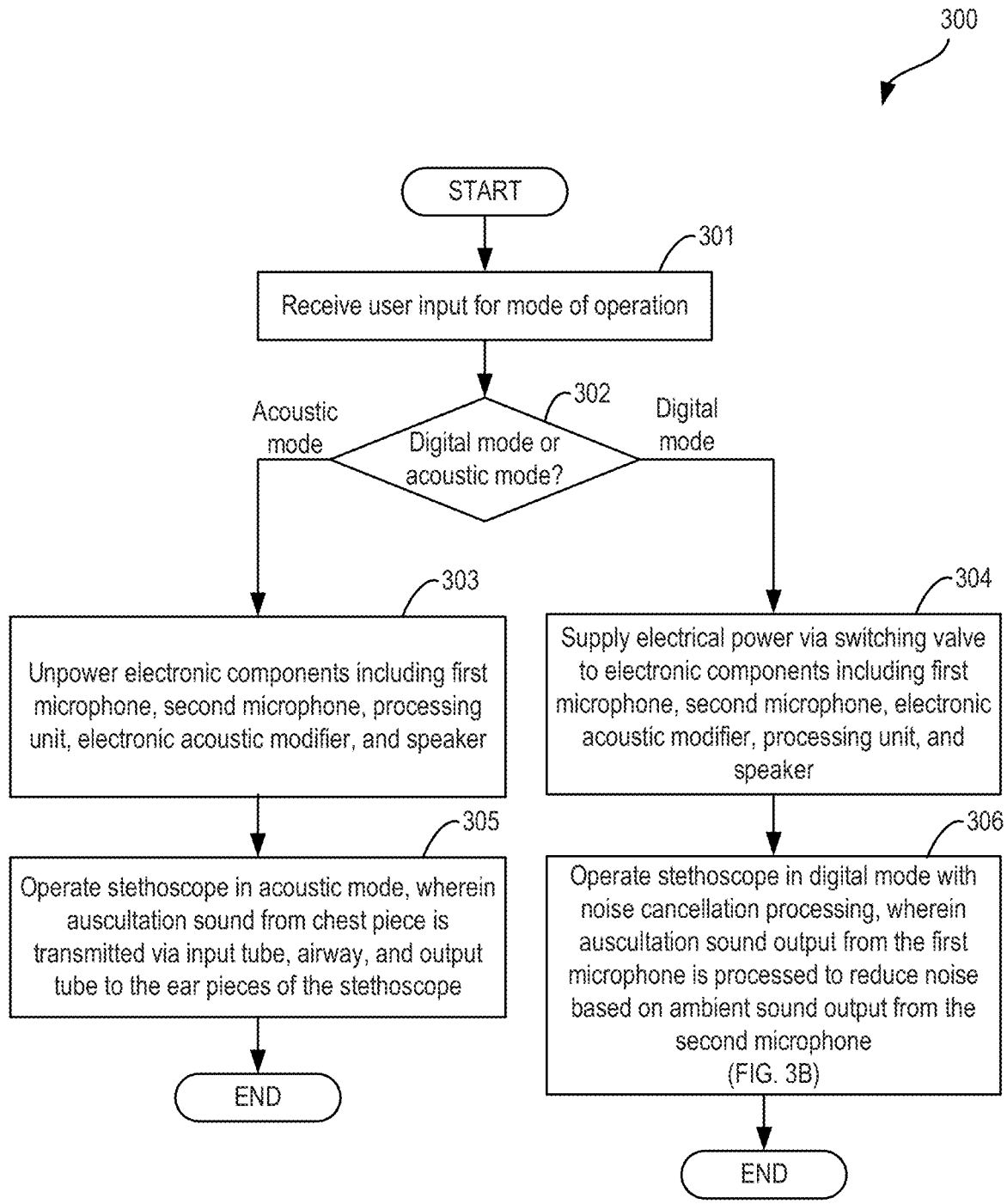
FIG. 3A is a high-level flow chart illustrating an example method for determining a mode of operation of a stethoscope with an electronic stethoscope device, according to an embodiment of the invention.

Next, FIG. 3A shows a high-level flow chart illustrating an example method 300 for operating an electronic stethoscope, such as the electronic stethoscope 200, including an electronic stethoscope device, such as the electronic stethoscope device 240. The method 300 is described with reference to FIGS. 2A-2D, and 5A-5E, however, the method may be applicable to other electronic stethoscopes without departing from the scope of the disclosure. At least portions of method shown in FIG. 3A may be performed via a human in cooperation with one or more of the systems of FIGS. 2A-2D, and FIGS. 5A-5E. In some examples, at least portions of method shown in FIG. 3A may be incorporated as executable instructions stored in non-transitory memory of a controller. In addition, some portions of the method may be performed via the controller transforming operating states of devices and actuators in the physical world.

The method 300 begins at 301. At 301, the method includes receiving a user input for a desired mode of operation of the electronic stethoscope. In some examples, the user, via a toggle switch, may change the operation of a switching valve, such as switching valve 246 or switching valve 546, between a digital mode and an acoustic mode. In some other embodiments, based on user input via a user interface of the electronic stethoscope device, for example, a processor, such as CPU 251 of the electronic stethoscope device at FIG. 2A or a processor of a PCB, such as module 502 at FIG. 5A may control operation of the switching valve (e.g., via an actuator).

Next, method 300 includes determining if the electronic stethoscope is to be operated in a digital mode or an acoustic mode. For example, if the user has toggled the switching valve to a closed position, the stethoscope is to be operated in a digital mode, and accordingly, the method 300 proceeds to 304. At 304, the method 300 includes supplying electrical power to one or more electronic components of the electronic stethoscope device via the switching valve. For example, the closure of switching valve may automatically establish electrical connections of the one or more electronic components with a power source, such a battery 266 or 566. As a result, the one or more electronic components are electrically powered when the stethoscope is operated in the digital mode. The one or more electronic components include but not limited to a first microphone (e.g., first microphone 262 or 562), a second microphone (e.g., second microphone 264 or 564), the processing unit (e.g., processing unit 251 or 551), the speaker (e.g., speaker 274 or 574), the wireless transceiver (e.g., transceiver 276), and the audio connector (e.g., connector 275).

Next, at 306, the method 300 includes operating the stethoscope in the digital mode with noise cancellation processing, wherein auscultation sounds are acquired by a chestpiece of the electronic stethoscope, and are perceived by the first microphone. An auscultation sound signal from the first microphone is the processed based on audio perceived by the second microphone as discussed below at FIG. 3B. In one example, active noise cancellation processing may be performed based on executable instructions stored in the electronic acoustic modifier the using the auscultation sound signal (output from the first microphone) and the audio signal(output from the second microphone).

Returning to 302, if the stethoscope is to be operated in an acoustic mode, the method 300 proceeds to 303. At 303, the method includes un-powering the electronic components of the electronic stethoscope. For example, if the user has toggled the switching valve to an open position, the acoustic mode is activated. When operating in the acoustic mode, due to the open position of the switching valve, electrical connection is severed between the power source and the various electronic components. As a result, the electronic components are unpowered.

Further, at 305, the method 300 includes operating the stethoscope in the acoustic mode, wherein the auscultation sounds from the chestpiece is transmitted from the input tube via the entire length of the airway in the first chamber 242 and the second chamber 244 and the opening of the switching valve. Further, due to the electronic components being unpowered, modification of the auscultation sounds are not based on audio signal perceived by the second microphone, instead, the electronic stethoscope device may include a first mechanical modifier (e.g., first mechanical acoustic modifier 252) and/or a second mechanical modifier (e.g., second mechanical acoustic modifier 256) for filtering the auscultation sounds.

Figure 3B:
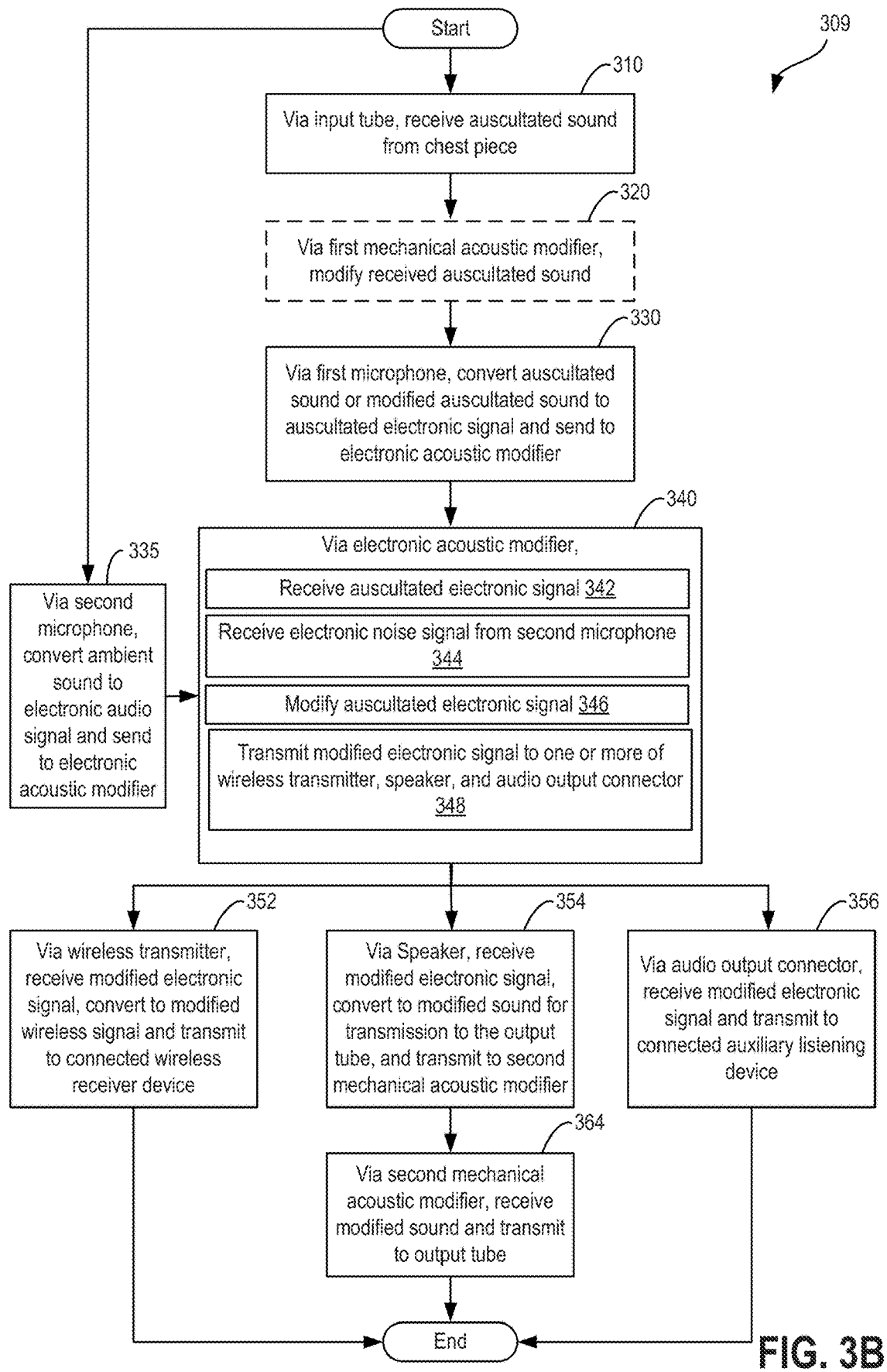
FIG. 3B is a high-level flow chart that shows the steps in using an electronic stethoscope device with noise cancellation, according to an embodiment of the invention.

FIG. 3B shows a high-level flow chart illustrating an example method 309 for operating the electronic stethoscope in the digital mode. The steps in using the electronic stethoscope device in the digital mode with noise cancellation and including optional components are shown in FIG. 3B, according to an embodiment of the invention. At least portions of method shown in FIG. 3B may be performed in cooperation with one or more of the systems of FIGS. 2A-2D, and FIGS. 5A-5E. In some examples, at least portions of method shown in FIG. 3B may be incorporated as executable instructions stored in non-transitory memory of a controller. In addition, some portions of the method may be performed via the controller transforming operating states of devices and actuators in the physical world.

In step 310, a stethoscope chestpiece picks up and sends auscultated sound to an input tube of an electronic stethoscope device. In step 320, an optional first mechanical acoustic modifier receives the auscultated sound and modifies the sound with mechanical acoustical modification, as described above. In step 330, a first microphone receives sound from the first mechanical acoustic modifier (or directly from the chestpiece for embodiments in which there is no first mechanical acoustic modifier), converts the sound to an auscultated electronic signal, and sends the auscultated electronic signal to an electronic acoustic modifier, which may be a standalone electronic component or firmware or software on a CPU. In step 335, an optional second microphone detects audio from the environment, converts the audio to an electronic audio signal, and sends the signal to the electronic acoustic modifier. Step 340 includes processing the auscultation electronic signal and the electronic audio signal via the electronic acoustic modifier. Accordingly, in step 342, the electronic acoustic modifier receives the auscultated electronic signal from the first microphone and in step 344, the electronic acoustic modifier receives the electronic audio signal from the second microphone (if there is a second microphone). Further, in step 346, the electronic acoustic modifier modifies the auscultated electronic signal with electronic acoustical modification (taking into account the electronic audio signal if it is available) to form a modified electronic signal, and in step 348, transmits the modified electronic signal. The modified electronic signal may be transmitted to one or more of a wireless transceiver, a speaker, and an audio output connector.

If the modified electronic signal is transmitted to a wireless transceiver, in step 352, the wireless transceiver receives the modified electronic signal, converts it to a modified wireless signal, and transmits the modified wireless signal. a peripheral wireless receiver device, (e.g., computer, cell phone, cloud application) receives the modified wireless signal, which is then available for further manipulation or analysis.

If the modified electronic signal is transmitted to a speaker, in step 354, the speaker receives the modified electronic signal and converts it to modified sound for transmission to the output tube. In step 364, an optional second mechanical acoustic modifier receives the modified sound, modifies the sound with mechanical acoustical modification, and sends the resulting sound to the output tube.

If the modified electronic signal is transmitted to an audio output connector, in step 356, the audio output connector receives the modified electronic signal for a direct wired connection to a peripheral device, such as a listening device configured to convert the modified electronic signal to sound or a computer or cell phone.

Figure 5A:
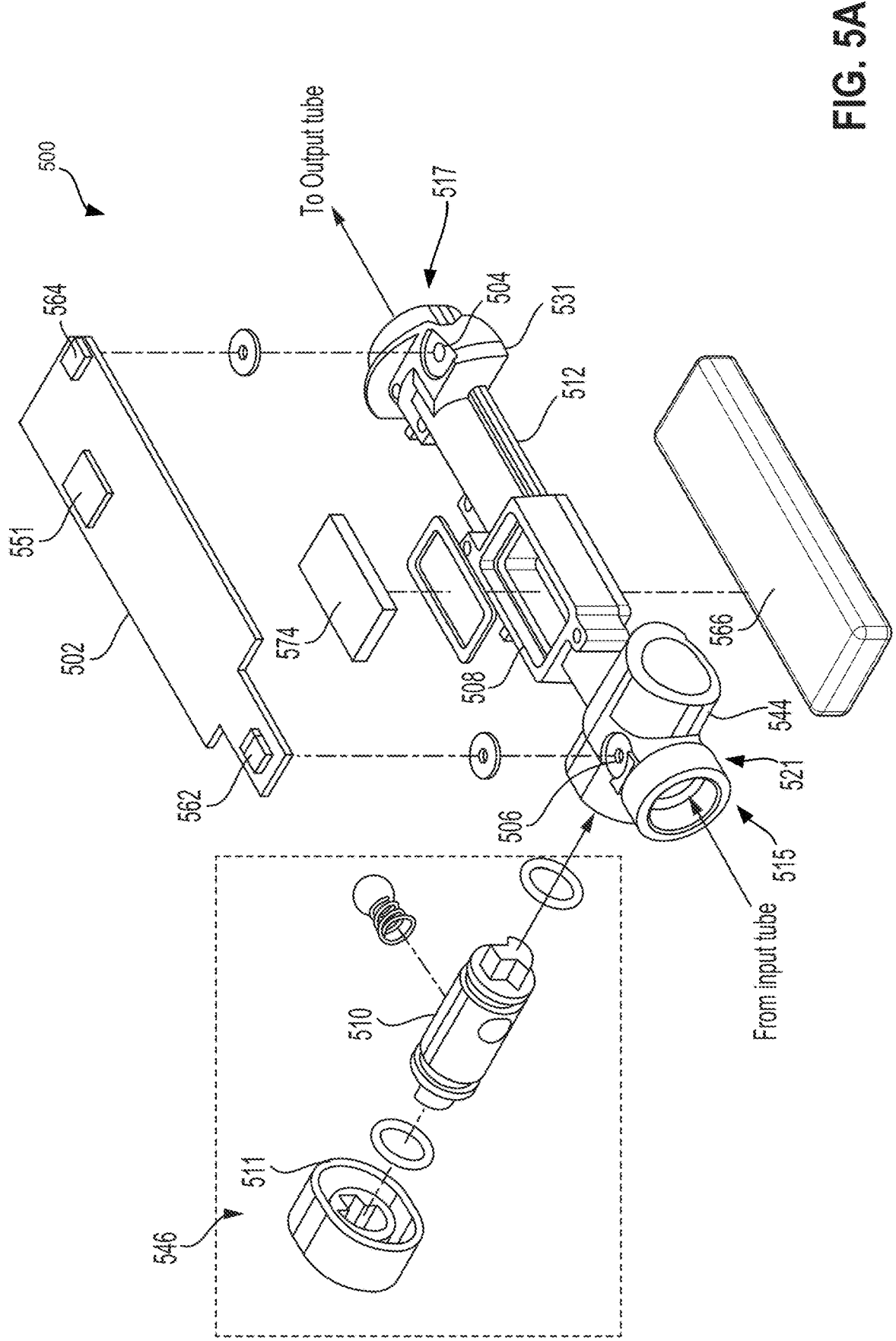
FIG. 5A shows an exploded perspective view of an example electronic stethoscope device, according to an embodiment of the invention.

FIGS. 5A-5E show various views of an embodiment of an electronic stethoscope device 500. Turning to FIG. 5A, it shows an exploded top perspective view of the electronic stethoscope device 500 that may be included in an electronic stethoscope, such as the electronic stethoscope of FIG. 2A. The electronic stethoscope device 500 may be similar to electronic stethoscope device 240 described at FIGS. 2B-2D. It may be noted that similarly numbered or similarly named components may function in a substantially similar manner.

The electronic stethoscope device 500 comprises a housing 512 that includes an airway for transmitting auscultation sounds received from a chestpiece of the electronic stethoscope. For example, at an input end 515 of the housing, the housing 512 may be coupled to an input tube, such as input tube 232, which is coupled to the chestpiece. The electronic stethoscope device 500 further comprises a module 502 that includes one or more electronic components for operating the electronic stethoscope in a digital mode. The module 502 may be a circuit board, for example. Module 502 includes a first microphone 562, a second microphone 564, and a processing unit 551. Module 502 further includes a wireless transceiver, such as wireless transceiver 276, and an audio output connector, such as audio output connector 275. In one embodiment, the processing unit 551 includes an electronic acoustic modifier, such as electronic acoustic modifier 254, for processing an auscultation signal received from the first microphone 562. In one example, processing the auscultation signal may include performing active noise cancellation based on an ambient audio signal received from the second microphone 564.

The electronic stethoscope device 500 comprises a speaker cavity 508 within the housing 512 for receiving a speaker 574. During operation of the electronic stethoscope in the digital mode, the speaker 574 may receive a processed auscultation signal from the electronic acoustic modifier, and output a modified sound signal to an output tube, such as the output tube 234, coupled to an output end 517 of the housing 512. In some examples, the output from the speaker 574 may be further modified by a mechanical acoustic modifier (not shown), such as the second mechanical acoustic modifier 256 discussed at FIG. 2B. The mechanical acoustic modifier for modifying the speaker output may be positioned towards the output end 517 within the airway enclosed by the housing 512.

Further, towards the input end 515, the housing 512 includes a valve enclosure 544 for receiving a switching valve assembly 546. Switching valve 546 is similar to switching valve 246 described at FIGS. 2B-2D. The switching valve 546 includes a valve body 510 and a valve cover 511. The valve body 510 may be inserted into the valve enclosure 544 such that a length of the valve body 510 is perpendicular to a length of the housing 512. The switching valve 546 may be toggled between an open position and a closed position by a user in order to operate the electronic stethoscope in an acoustic mode (open position) or a digital mode (closed position). When assembled, the valve body 510 of the switching valve 546 is within the airway.

When the switching valve 546 is adjusted to the open position, the electronic stethoscope is operated in the acoustic mode wherein the auscultation sound is transmitted from the chestpiece to the input tube and subsequently transmitted through the airway via an opening caused by the open position of the switching valve. That is, when the switching valve 546 is open, the airway is continuous along the length of the housing 512, and the airway is in fluid communication with the input tube and the output tube. The airway is depicted in the cross sectional view in FIG. 5D. The auscultation sound from the chestpiece, after passing through the airway, are delivered to ear pieces, such as ear pieces 280, via the output tube.

When the switching valve 546 is in the open position, all of the electronic components are unpowered. For example, the electronic stethoscope device 500 includes a battery 566 as a power source for electrically powering the electronic components (that is, the first microphone 562, the second microphone 564, the processing unit 551, the speaker 574, the wireless transceiver, and the audio connector interface). When the switching valve 546 is in the open position, respective electrical connections of the electronic components with a power source, such as battery 566, are not established, and therefore, the electronic components are unpowered. The electronic components that are unpowered in the acoustic mode include but are not limited to the first microphone 562, the second microphone 564, the processing unit 551, the speaker 574, the wireless transceiver, and the audio output interface. Thus, filtering of the auscultation sound, when operated in the acoustic mode, is performed by using one or more mechanical acoustic filters (not shown), such as first mechanical acoustic modifier 252 and/or second mechanical acoustic modifier 256. In one example, as discussed above with respect to FIG. 2B, the first mechanical acoustic modifier may be positioned in an input portion 521 of the airway between the input tube and the switching valve 546, and the second mechanical acoustic modifier may be positioned towards the output end 517 at a location between a speaker cavity and the output tube. Examples of mechanical filters that may be utilized as the first and/or the second mechanical acoustic modifiers are described at FIGS. 4A-4E.

When the switching valve 546 is adjusted to a closed position, the electronic stethoscope is operated in the digital mode, wherein the auscultation sound is processed by the processing unit 551 to generate a noise cancelled output, which is delivered to one or more audio output devices coupled to the electronic stethoscope device and/or a wireless transceiver. Further, in the digital mode, the auscultation sound is not transmitted from the input tube through the airway to the output tube due to closure of the airway by the switching valve. Rather, the auscultation sound is transmitted from the input tube through a first port 506 to the first microphone 562. That is, when operated in the digital mode, the airway is not continuous along the length of the housing and is interrupted by the closure of the switching valve 546. Further still, when the switching valve 546 is in the closed position, all the electronic components of the electronic stethoscope device 500 are electrically powered. In one example, closure of the switching valve establishes electrical connection of the electronic components with the battery 566, which results in current flow through one or more circuits electrically powering the electronic components of the electronic stethoscope, the electronic components including but not limited to the first microphone 562, the second microphone 564, the processing unit 551, the speaker 574, the wireless transceiver, and the audio output interface.

As discussed above, the first microphone 562 receives auscultation sounds via the input tube coupled to the housing 512. In particular, the housing 512 includes the first port 506 in fluid communication with the input portion 521 of the airway, and the first microphone 562 receives auscultation sounds via the first port 506. The first port 506 is fluidly coupled to the input portion 521 of the airway at a location downstream of the switching valve 546, downstream in a direction from an input end 515 to an output end 517 of the housing 512. Further, when present, the first mechanical modifier may be disposed in the input portion 521 such that the auscultation sound passes through the first mechanical acoustic modifier, and thus, in some examples, the auscultation sound from the chestpiece is modified (e.g., filtered) by the first mechanical acoustic modifier prior to being input to the first microphone 562.

The second microphone 564 receives ambient sounds from the environment via a second port 504, which is in fluid communication with the ambient, and generates an ambient sound signal. The ambient sound signal from the second microphone 564 is then fed as an input to the electronic acoustic modifier which performs noise cancellation processing of the auscultation signal from the first microphone 562 based on the ambient sound signal from the second microphone 564. In order to ensure that auscultation sounds are not perceived by the second microphone 564 and to reduce feeding back auscultation sounds as ambient audio, the second microphone is mechanically isolated from the airway, the speaker 574, and the first microphone 562. In order to mechanically isolate the second microphone 564 from the first microphone 562, the second microphone 564 is positioned towards the output end 517 of the housing 512, opposite to the input end 515 towards which the first microphone is positioned. Further, the second port 504 that feeds ambient sound to the second microphone 564 is mechanically separated from the airway by a thickness of a wall of the housing 512. Further, as the speaker chamber 508 and hence, the speaker 574 located in the chamber 508 are fluidly coupled to the airway, the thickness of the wall of the housing 512 also provides mechanical isolation of the second port 504 and the second microphone 564 from the speaker 574.

Further, an input length of the input portion 521 of the airway between the switching valve 546 and the input end 515 is smaller than an output length of an output portion of the airway between the switching valve 546 and the output end 517. The greater length of the output portion of the airway allows the speaker 574 to be acoustically coupled to the airway while providing a threshold distance between the speaker 574 and the second microphone 564 that reduces coupling of an output from the speaker with the input of the second microphone 564. The greater length of the output portion of the airway functions in conjunction with the mechanical isolation provided by the housing wall between the airway and the second microphone 564.

In one example, as shown in FIGS. 5A-5D, the second port 504 may be disposed in an extended portion 531 of the housing 512 to further separate the second port 504 from the airway and the speaker 574. Due to the extension of the housing 512, the thickness of the housing wall that separates the second port 504 and the second microphone 564 from the airway and the speaker 574 is greater, which reduces coupling of the auscultation sound output from the speaker and/or or transmitting through the airway with the input to the second microphone 564.

Further, the first microphone 562 is positioned directly above a top surface of the first port 506 and the second microphone 564 is positioned directly above a top surface of the second port 504, and thus, by disposing the second port 504 in the extended portion 531 of the housing 512 and positioning the second microphone 564 directly above the second port, the first and the second microphone are also further separated from each other.

Further still, during the digital mode, the closure of the switching valve 546 blocks transmission of the auscultation sound through the airway from the input tube to the output tube, and as such, the closed position of the valve provides additional mechanical isolation. For example, auscultation sound perceived by the second microphone 564 due to direct auscultation sound transmission in the airway from the input tube may be reduced by the closure of the switching valve 546.

Furthermore, the first microphone 562 is also mechanically isolated from the speaker 574 by closure of the switching valve 546. Since the speaker 574 is positioned away from the input end 515 and between the switching valve and the output end 517, output from the speaker does not feedback into the first microphone 562 that receives auscultation sound acquired by the chestpiece.

Figure 5B:
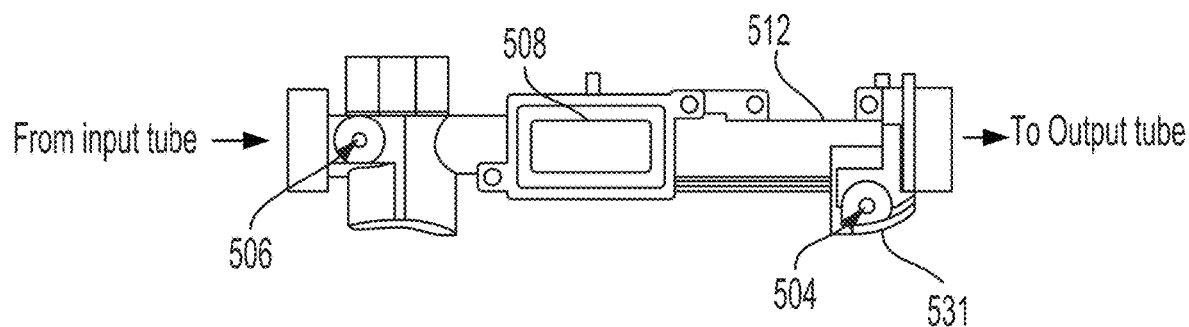
FIG. 5B shows a top view of a housing of the electronic stethoscope device of FIG. 5A, according to an embodiment of the invention.
Figure 5C:
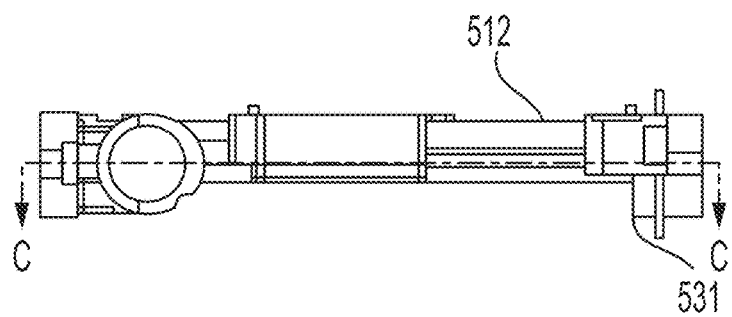
FIG. 5C shows a side view of the housing of the electronic stethoscope device of FIG. 5A, according to an embodiment of the invention.
Figure 5D:
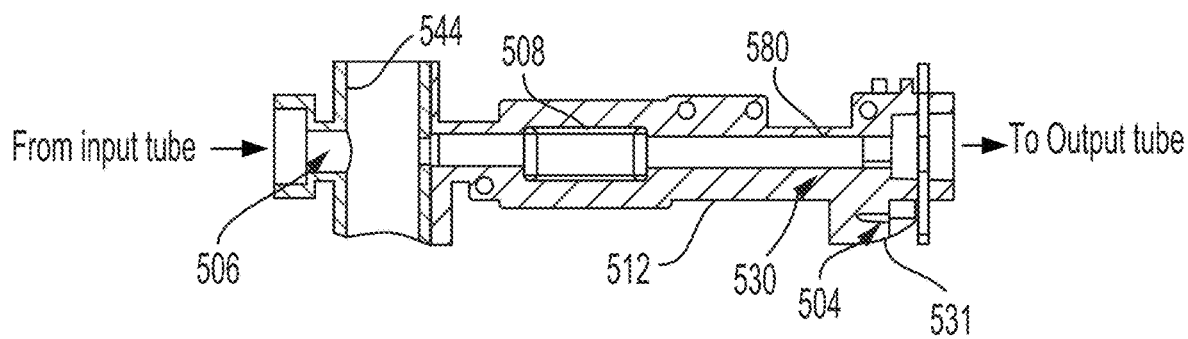
FIG. 5D shows a cross-sectional view of the housing of the electronic stethoscope device of FIG. 5A, according to an embodiment of the invention.

The relative positions of the first port 506 (fluidly communicating auscultation sounds from the input portion of the airway to the first microphone 562) and the second port 504 (fluidly communicating ambient sounds from the environment to the second microphone 564) are also shown in FIG. 5B, which shows a top view of the housing 512. While the first port 506 is positioned along a length of the airway between the input tube and the switching valve 546, and fluidly communicates with the input portion 521 of the airway, the second port 504 is positioned separated from the airway by a housing wall 530, as shown in the cross-sectional view in FIG. 5D. Further, a thickness of a portion the housing wall 530 separating the second port 504 and the airway (indicated by 580 in FIG. 5D) may be greater than a thickness of the remaining portion of the housing 512. In some embodiments, a thickness of an entire side of the housing wall on which the second port is positioned may be greater so as to separate the second port 504 from the airway and the speaker 574. Further, the first port 506 and the second port 504 are positioned on different planes. In this way, by mechanically isolating the first port 506, the first microphone 562, the airway, and the speaker 574 from the second port 504 and the second microphone 564, via the housing wall thickness and relative positioning towards opposite ends of the housing, an amount of auscultation sound feeding into the second microphone is significantly reduced. As a result, noise-cancellation processing performed by the electronic acoustic modifier is improved.

Figure 5E:
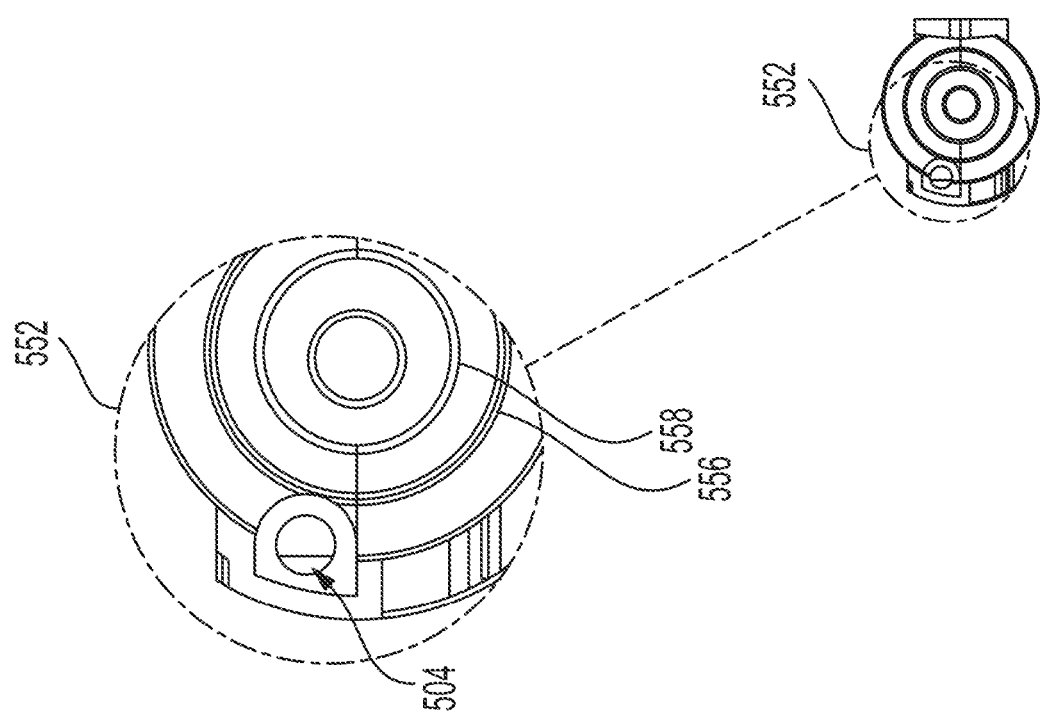
FIG. 5E shows an enlarged view of a portion of a right side of the housing of the electronic stethoscope device of FIG. 5A, according to an embodiment of the invention.

FIG. 5E shows an enlarged view of a portion 552 of a right side view of the housing 512. The enlarged view shows the second port 504 fluidly coupled to the environment, an inner side 558 of the housing wall and an outer side 556 of the housing wall when viewed from the right side into the output end.

The above described electronic stethoscope provides a technical effect of reduced auscultation sound coupling between the speaker and the first and the second microphones. The mechanical isolation of the second microphone from the airway, the speaker, and the first microphone reduces unwanted auscultation sound feedback into the second microphone. Further, the first and the second mechanical acoustic modifiers provide additional mechanical filtration of the auscultation sound. Overall, the positioning of the first and the second microphones with respect to the airway and the speaker reduces unwanted intermixing of the auscultation sound (before and after processing) and ambient audio (that is, ambient noise) during the digital mode of operation. As a result, noise cancellation processing performed by the electronic acoustic modifier is improved, and in conjunction with the mechanical acoustic modifiers, clarity and specificity of auscultation sounds delivered to the user is improved. Further, by ensuring that the electronic components are only turned on when the switching valve is closed, any interference of the electronic components during acoustic mode of operation is reduced.

An embodiment of the electronic stethoscope device comprises: an airway in acoustic communication with a chestpiece of a stethoscope; a first microphone for receiving auscultation sound from the chestpiece via a first port, the first port in acoustic communication with a first portion of the airway; a second microphone for receiving ambient noise via a second port in acoustic communication with ambient air, the second microphone mechanically isolated from the airway; a switching valve disposed within the airway, the switching valve when operated in an open position causes each of the first microphone and the second microphone to be electrically powered, and when operated in a closed position causes each of the first microphone and the second microphone to be unpowered; and a control unit in electrical communication with the first microphone and the second microphone, the control unit including a processor and a non-transitory memory, the non-transitory memory including instructions that when executed cause the processor to: when the switching valve is in the closed position, receive a first input from the first microphone and a second input from the second microphone; perform noise cancellation on the first input based on the second input; and output a noise-cancelled output signal to one or more audio interface outputs and/or a wireless transceiver.

In a first example of the device, the electronic stethoscope device further comprises a speaker in acoustic communication with a second portion of the airway via a speaker chamber, the second portion between the switching valve and an output end of the airway; and wherein when the switching valve is operated in the closed position, the speaker is electrically powered and the speaker receives the noise-cancelled output signal from the control unit.

In a second example of the device, which optionally includes the first example, the electronic stethoscope device further comprises: a first mechanical acoustic modifier disposed within the first portion of the airway, the first mechanical acoustic modifier configured to receive the auscultated sound from the input tube and to apply mechanical acoustic modification to the auscultated sound.

In a third example of the device, which optionally includes one or more of the first and the second examples, the electronic stethoscope device, further comprises: a second mechanical acoustic modifier disposed within the second portion of the airway, the first mechanical acoustic modifier configured to receive a sound output from a speaker and to apply mechanical acoustic modification to the sound output.

In a fourth example of the device, which optionally includes one or more of each of the first through third examples, the airway is enclosed within a housing, and wherein the second microphone is mechanically isolated from the airway by a wall of the housing.

In a fifth example of the device, which optionally includes one or more of each of the first through fourth examples, the second microphone is disposed within an extended portion of the housing.

In a sixth example of the device, which optionally includes one or more of each of the first through fifth examples, the electronic stethoscope device further comprises a battery configured to supply power to at least the first microphone, the second microphone, the speaker, and the control unit.

In a seventh example of the device, which optionally includes one or more of each of the first through sixth examples, a first length of the first portion of the airway is less than a second length of the second portion of the airway.

In an eight example of the device, which optionally includes one or more of each of the first through seventh examples, the wireless transceiver is configured to receive the noise cancelled output signal, to convert noise-cancelled output signal to a modified wireless signal, and to wirelessly transmit the modified wireless signal from the electronic stethoscope device.

In a ninth example of the device, which optionally includes one or more of each of the first through eighth examples, the wireless transceiver is further configured to receive signals from one or more peripheral devices.

An embodiment of a method an electronic stethoscope, comprises: during a first operating mode, when a switching valve position is in a closed position, supplying electrical power to a first microphone, a second microphone, and a processing unit; converting, via the first microphone, a first audio signal from a chestpiece of the electronic stethoscope to a first electronic signal; converting, via the second microphone, a second audio signal from ambient to a second electronic noise signal; receiving, via the processing unit, the first electronic signal and the second electronic noise signal; generating, via the processing unit, a noise-cancelled output using the first and the second electronic signals; and transmitting the noise-cancelled output to one or more audio rendering devices; during a second operating mode, when the switching valve position is in an open position, not supplying electrical power to the first microphone, the second microphone, and the processing unit while transmitting the first audio signal from the chestpiece to an output tube via an opening in an airway disposed between the chestpiece and the output tube, the opening resulting from the open position of the switching valve; and wherein, the first microphone is in acoustic communication with a portion of the airway between the chestpiece and the switching valve; and wherein the second microphone is mechanically isolated from the airway.

In a first example of the method, the one or more sound rendering devices includes a speaker, the speaker acoustically coupled to a second portion of the airway between the switching valve and the output tube, during the first operating mode, supplying electrical power to the speaker, and during the second operating mode, not supplying electrical power to the speaker.

In a second example of the method, which optionally includes the first example, mechanically filtering, via a first mechanical acoustic modifier, the first audio signal prior to transmitting to the first microphone.

In a third example of the method, which optionally includes one or more of the first and the second examples, mechanically filtering the noise cancelled output via a second mechanical acoustic filter.

An embodiment of a method of using an electronic stethoscope device comprises the steps of: providing a stethoscope with an electronic stethoscope device, using the stethoscope to auscultate a patent to obtain auscultated sound, and sending the auscultated sound to an input tube of the electronic stethoscope device; optionally providing a first mechanical acoustic modifier, and allowing the first mechanical acoustic modifier to receive the auscultated sound and to modify the auscultated sound with mechanical acoustical modification to form modified auscultated sound; providing a first microphone, and allowing the first microphone to receive either the auscultated sound or the modified auscultated sound and to convert either the auscultated sound or the modified auscultated sound to an auscultated electronic signal; providing an electronic acoustic modifier, and allowing the electronic acoustic modifier to receive the auscultated electronic signal and to modify the auscultated electronic signal with electronic acoustical modification to form a modified electronic signal; optionally providing an optional second microphone, allowing the second microphone to detect noise and to convert the noise to an electronic noise signal, and allowing the electronic acoustic modifier to further modify the auscultated electronic signal using active noise cancellation and/or single channel noise reduction that takes into account the electronic noise signal to form the modified electronic signal; optionally providing a wireless transceiver and allowing the wireless transceiver to receive the modified electronic signal, to convert the modified electronic signal to a modified wireless signal, and to transmit the modified wireless signal; optionally providing a speaker and allowing the speaker to receive the modified electronic signal and to convert the modified electronic signal to modified sound for transmission to earpieces of the stethoscope; and providing an optional second mechanical acoustic modifier and allowing the second mechanical acoustic modifier to receive the modified sound and to modify the modified sound further with mechanical acoustical modification to form a more modified sound for transmission to the earpieces of the stethoscope. A first example of the method comprises providing a wireless receiver device and allowing the wireless receiver device to receive the modified wireless signal. A second example of the method optionally includes the first example, and further comprises providing an audio output connector and allowing the audio output connector to receive the modified electronic signal.

The disclosure also provides support for an electronic stethoscope device, comprising: an airway disposed between an input tube in acoustic communication with a stethoscope chestpiece and an output tube, the airway comprising a first chamber adjacent to the input tube and a second chamber adjacent to the output tube, the first chamber and the second chamber configured to be in acoustic communication with one another, the airway permitting acoustic transmission of auscultated sound between the input tube and the output tube, wherein the auscultated sound is sound detected by the stethoscope chestpiece from a patient's body, a switching valve disposed within the airway between the first chamber and the second chamber, the switching valve configured to have an open position and a closed position, wherein the open position permits acoustic transmission of the auscultated sound between the first chamber and the second chamber and corresponds to an acoustic mode of operation for the electronic stethoscope device, and the closed position blocks the acoustic transmission of the auscultated sound between the first chamber and the second chamber and corresponds to a digital mode of operation for the electronic stethoscope device, a first microphone disposed in the airway, the first microphone configured to receive the auscultated sound and to convert the auscultated sound into an auscultated electronic signal, and an electronic acoustic modifier in electrical communication with the first microphone, the electronic acoustic modifier configured to receive the auscultated electronic signal, to apply electronic acoustic modification to the auscultated electronic signal to form a modified electronic signal, and to transmit the modified electronic signal, and a computer processing unit configured to receive and transmit electronic signals from one or more of the first microphone and the electronic acoustic modifier. In a first example of the system, the system further comprises: a first mechanical acoustic modifier disposed in the first chamber, the first mechanical acoustic modifier configured to receive the auscultated sound from the input tube and to apply mechanical acoustic modification to the auscultated sound. In a second example of the system, optionally including the first example, the system further comprises: a speaker disposed in the second chamber of the airway, the speaker in electrical communication with the electronic acoustic modifier, the speaker configured to produce no sound when the electronic stethoscope device is in the acoustic mode of operation and to convert the modified electronic signal to modified sound for transmission to the output tube when the electronic stethoscope device is in the digital mode of operation. In a third example of the system, optionally including the first and second examples, the system further comprises: a wireless transceiver in electrical communication with the electronic acoustic modifier, the wireless transceiver configured to receive the modified electronic signal, to convert the modified electronic signal to a modified wireless signal, and to wirelessly transmit the modified wireless signal from the electronic stethoscope device. In a fourth example of the system, optionally including the first through third examples, the wireless transceiver is also configured to receive signals from one or more peripheral devices. In a fifth example of the system, optionally including the first through fourth examples, the system further comprises: a second mechanical acoustic modifier in the second chamber and adjacent to the output tube, the second mechanical acoustic modifier configured to receive the modified sound from the speaker and to apply mechanical acoustic modification to the modified sound as the modified sound travels into the output tube. In a sixth example of the system, optionally including the first through fifth examples, the switching valve further comprises an on/off switch for electrical components of the electronic stethoscope device, wherein, in the open position, the electrical components are on, and, in the closed position, the electrical components are off. In a seventh example of the system, optionally including the first through sixth examples, the system further comprises: a second microphone configured to detect audio from outside the electronic stethoscope device and to convert the audio into an electronic audio signal, wherein the electronic acoustic modifier is configured to receive the electronic audio signal from the second microphone and to use the electronic audio signal in modifying the auscultated electronic signal to form the modified electronic signal. In an eighth example of the system, optionally including the first through seventh examples, the second microphone is mechanically isolated from at least the airway and the speaker. In a ninth example of the system, optionally including the first through eighth examples, the mechanical isolation of the second microphone is provided by a housing wall enclosing the airway.

The disclosure also provides support for an electronic stethoscope, comprising: a control unit including a first microphone, a second microphone, and an electronic acoustic modifier, an airway between an input tube and an output tube, the airway including a switching valve to switch between a digital mode of operation and an acoustic mode of operation of the electronic stethoscope, a chestpiece coupled to the input tube, wherein the second microphone is mechanically isolated from the airway, wherein during the acoustic mode, the control unit is unpowered, and wherein during the digital mode, the control unit is electrically powered, and the electronic acoustic modifier generates a modified auscultation sound output based on a first auscultation sound input from the first microphone and a second audio input from the second microphone, and transmits the modified auscultation sound output to one or more audio interface outputs and/or a wireless transceiver. In a first example of the system, the system further comprises: a speaker in electrical communication with the electronic acoustic modifier, wherein during the acoustic mode, the speaker is unpowered, and wherein during the digital mode, the speaker is electrically powered and receives the modified auscultation sound output from the electronic acoustic modifier, and transmits an amplified sound output to the output tube. In a second example of the system, optionally including the first example, during the digital mode, the switching valve is in a closed position, and wherein during the acoustic mode, the switching valve is in an open position. In a third example of the system, optionally including the first and second examples, a first port to the first microphone and a second port to the second microphone are positioned on opposite ends of a length of a housing of the airway, the first port fluidly coupled to an input portion of the airway downstream of the switching valve in a direction from an input end to an output end of the housing, the input portion receiving auscultation sound acquired by the chestpiece, and the second port fluidly coupled to ambient and not coupled to the airway. In a fourth example of the system, optionally including the first through third examples, the second port is mechanically isolated from the airway by a thickness of a wall of the housing.

Although the invention has been described and illustrated in the foregoing illustrative embodiments, it is understood that the present disclosure has been made only by way of example, and that numerous changes in the details of implementation of the invention can be made without departing from the spirit and scope of the invention. Features of the disclosed embodiments can be combined and rearranged in various ways.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

FIGS. 5A-5E show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An electronic stethoscope device, comprising:
an airway disposed between an input tube in acoustic communication with a stethoscope chestpiece and an output tube, the airway comprising a first chamber adjacent to the input tube and a second chamber adjacent to the output tube, the first chamber and the second chamber configured to be in acoustic communication with one another, the airway permitting acoustic transmission of auscultated sound between the input tube and the output tube, wherein the auscultated sound is sound detected by the stethoscope chestpiece from a patient's body;
a switching valve disposed within the airway between the first chamber and the second chamber, the switching valve configured to have an open position and a closed position, wherein the open position permits acoustic transmission of the auscultated sound between the first chamber and the second chamber and corresponds to an acoustic mode of operation for the electronic stethoscope device, and the closed position blocks the acoustic transmission of the auscultated sound between the first chamber and the second chamber and corresponds to a digital mode of operation for the electronic stethoscope device;
a first microphone disposed in the airway, the first microphone configured to receive the auscultated sound and to convert the auscultated sound into an auscultated electronic signal; and
an electronic acoustic modifier in electrical communication with the first microphone, the electronic acoustic modifier configured to receive the auscultated electronic signal, to apply electronic acoustic modification to the auscultated electronic signal to form a modified electronic signal, and to transmit the modified electronic signal; and
a computer processing unit configured to receive and transmit electronic signals from one or more of the first microphone and the electronic acoustic modifier;
a second microphone configured to detect audio from outside the electronic stethoscope device and to convert the audio into an electronic audio signal, wherein the electronic acoustic modifier is configured to receive the electronic audio signal from the second microphone and to use the electronic audio signal in modifying the auscultated electronic signal to form the modified electronic signal; and
a first port to the first microphone and a second port to the second microphone, the first port fluidly coupled to an input portion of the airway downstream of the switching valve in a direction from an input end to an output end of a housing, the input portion receiving the auscultated sound, and the second port fluidly coupled to ambient and not coupled to the airway.

2. The electronic stethoscope device of claim 1, further comprising a first mechanical acoustic modifier disposed in the first chamber, the first mechanical acoustic modifier configured to receive the auscultated sound from the input tube and to apply mechanical acoustic modification to the auscultated sound.

3. The electronic stethoscope device of claim 1, further comprising a speaker disposed in the second chamber of the airway, the speaker in electrical communication with the electronic acoustic modifier, the speaker configured to produce no sound when the electronic stethoscope device is in the acoustic mode of operation and to convert the modified electronic signal to modified sound for transmission to the output tube when the electronic stethoscope device is in the digital mode of operation.

4. The electronic stethoscope device of claim 3, further comprising a second mechanical acoustic modifier in the second chamber and adjacent to the output tube, the second mechanical acoustic modifier configured to receive the modified sound from the speaker and to apply mechanical acoustic modification to the modified sound as the modified sound travels into the output tube.

5. The electronic stethoscope device of claim 1, further comprising a wireless transceiver in electrical communication with the electronic acoustic modifier, the wireless transceiver configured to receive the modified electronic signal, to convert the modified electronic signal to a modified wireless signal, and to wirelessly transmit the modified wireless signal from the electronic stethoscope device.

6. The electronic stethoscope device of claim 5, wherein the wireless transceiver is also configured to receive signals from one or more peripheral devices.

7. The electronic stethoscope device of claim 1, wherein the switching valve further comprises an on/off switch for electrical components of the electronic stethoscope device, and wherein, in the open position, the electrical components are off, and, in the closed position, the electrical components are on.

8. The electronic stethoscope device of claim 1, wherein the second microphone is mechanically isolated from at least the airway and a speaker disposed in the second chamber.

9. The electronic stethoscope device of claim 8, wherein the mechanical isolation of the second microphone is provided by a housing wall enclosing the airway.

10. An electronic stethoscope, comprising:
a control unit including a first microphone, a second microphone, and an electronic acoustic modifier;
an airway between an input tube and an output tube, the airway including a switching valve to switch between a digital mode of operation and an acoustic mode of operation of the electronic stethoscope; and
a chestpiece coupled to the input tube;
wherein the second microphone is mechanically isolated from the airway;
wherein, during the acoustic mode of operation, the control unit is unpowered; and
wherein, during the digital mode of operation, the control unit is electrically powered, and the electronic acoustic modifier generates a modified auscultation sound output based on a first auscultation sound input from the first microphone and a second audio input from the second microphone, and transmits the modified auscultation sound output to one or more audio interface outputs and/or a wireless transceiver; and
further comprising a first port to the first microphone and a second port to the second microphone, the first port fluidly coupled to an input portion of the airway downstream of the switching valve in a direction from an input end to an output end of a housing, the input portion receiving auscultation sound acquired by the chestpiece, and the second port fluidly coupled to ambient and not coupled to the airway.

11. The electronic stethoscope of claim 10, further comprising a speaker in electrical communication with the electronic acoustic modifier; wherein, during the acoustic mode, the speaker is unpowered; and wherein, during the digital mode, the speaker is electrically powered and receives the modified auscultation sound output from the electronic acoustic modifier, and transmits an amplified sound output to the output tube.

12. The electronic stethoscope of claim 10, wherein, during the digital mode of operation, the switching valve is in a closed position; and wherein, during the acoustic mode of operation, the switching valve is in an open position.

13. The electronic stethoscope of claim 10, wherein the second port is mechanically isolated from the airway by a thickness of a wall of the housing.

\* \* \* \* \*